(12) United States Patent
Birkner et al.

(10) Patent No.: US 12,186,018 B2
(45) Date of Patent: Jan. 7, 2025

(54) PATIENT-INDUCED TRIGGER OF A MEASUREMENT FOR OPHTHALMIC DIAGNOSTIC DEVICES

(71) Applicant: Alcon Inc., Fribourg (CH)

(72) Inventors: Sascha Birkner, Berlin (DE); Martin Gründig, Rangsdorf (DE); Peter Zieger, Berlin (DE)

(73) Assignee: Alcon Inc., Fribourg (CH)

( * ) Notice: Subject to any disclaimer, the term of this patent is extended or adjusted under 35 U.S.C. 154(b) by 517 days.

(21) Appl. No.: 17/025,452

(22) Filed: Sep. 18, 2020

(65) Prior Publication Data

US 2021/0093193 A1   Apr. 1, 2021

Related U.S. Application Data

(60) Provisional application No. 62/906,755, filed on Sep. 27, 2019.

(51) Int. Cl.
*A61B 3/10* (2006.01)
*A61B 3/02* (2006.01)
(Continued)

(52) U.S. Cl.
CPC ............ *A61B 3/12* (2013.01); *A61B 3/102* (2013.01); *A61B 3/113* (2013.01); *A61B 3/145* (2013.01);
(Continued)

(58) Field of Classification Search
CPC ........... A61B 3/103; A61B 3/14; A61B 3/113; A61B 3/1225; A61B 3/024; A61B 3/032; A61B 3/18; A61B 3/1015; A61B 3/107; A61B 3/14542; A61B 5/4266; A61B 3/008
(Continued)

(56) References Cited

U.S. PATENT DOCUMENTS 10,524,657 B2   1/2020   Jeglorz
2005/0225725 A1*  10/2005  Warden ............... A61B 3/0075
                                                    351/200
(Continued)

FOREIGN PATENT DOCUMENTS

CN   103501406 A   *  1/2014   ............ G06F 3/013
JP   2002306417 A    10/2002
(Continued)

*Primary Examiner* — Dawayne Pinkney

(57) ABSTRACT

Systems and methods for tracking the position and condition of an eye during an ophthalmic procedure include an ophthalmic device configured to measure characteristics of an eye, an eye tracker configured to capture a stream of eye images, and a logic device configured to analyze the stream of images to determine whether the eye is fixating on a target object, detect a predetermined blink sequence in the first stream of images, delay for a predetermined tear stabilization period, start a stable tear film interval, and during the stable tear film interval, capture at least one measurement of the eye using the ophthalmic device when the eye is fixating. The blink sequence may include a plurality of blinks in succession and the detection of the blink sequence may include processing the images through a neural network trained to detect an open eye and/or a closed eye.

20 Claims, 12 Drawing Sheets

(51) Int. Cl.
*A61B 3/113* (2006.01)
*A61B 3/12* (2006.01)
*A61B 3/14* (2006.01)
*G06T 7/00* (2017.01)
*G06T 7/20* (2017.01)
*G06T 7/73* (2017.01)
*G06V 40/19* (2022.01)

(52) U.S. Cl.
CPC ............ *G06T 7/0012* (2013.01); *G06T 7/20* (2013.01); *G06T 7/73* (2017.01); *G06V 40/19* (2022.01); *G06T 2207/10016* (2013.01); *G06T 2207/10101* (2013.01); *G06T 2207/20081* (2013.01); *G06T 2207/20084* (2013.01); *G06T 2207/30041* (2013.01)

(58) Field of Classification Search
USPC ....... 351/210, 206, 200, 205, 209, 221–223, 351/245–246, 212, 208, 247; 600/356, 600/346, 476, 425
See application file for complete search history.

(56) References Cited

U.S. PATENT DOCUMENTS

| | | | | |
|---|---|---|---|---|
| 2009/0189830 | A1* | 7/2009 | Deering | G09G 3/02 345/1.3 |
| 2009/0219405 | A1 | 9/2009 | Kaneda | |
| 2011/0149239 | A1* | 6/2011 | Neal | A61B 3/103 351/205 |
| 2011/0261320 | A1* | 10/2011 | Hacker | A61B 3/152 351/210 |
| 2013/0010096 | A1* | 1/2013 | S | G06F 3/013 348/78 |
| 2017/0071465 | A1* | 3/2017 | Neal | A61B 3/1015 |
| 2017/0293356 | A1* | 10/2017 | Khaderi | G06F 3/147 |

FOREIGN PATENT DOCUMENTS

| | | | | |
|---|---|---|---|---|
| JP | 2009211180 A | 9/2009 | | |
| JP | 2017516508 A | 6/2017 | | |
| JP | 2018512665 A | 5/2018 | | |
| JP | 2019017988 A | 2/2019 | | |
| WO | WO-2006031909 A2 * | 3/2006 | ............ | A61B 3/101 |
| WO | 2015143073 A1 | 9/2015 | | |
| WO | 2016151581 A1 | 9/2016 | | |
| WO | 2019141750 A1 | 7/2019 | | |

* cited by examiner

PATIENT-INDUCED TRIGGER OF A MEASUREMENT FOR OPHTHALMIC DIAGNOSTIC DEVICES

BACKGROUND

Field of the Disclosure

The present disclosure relates generally to eye diagnostic systems and methods, and more particularly, for example, to systems and methods for tracking the position, orientation and/or condition of an eye in imaging, diagnostic and/or surgical systems.

Description of Related Art

A wide variety of ophthalmic devices are used to image, measure, diagnose, track, surgically correct and/or surgically repair a patient's eyes. The operation of an ophthalmic device such as a topography device, a keratometry device, a wavefront analyzer or another device that measures aspects of the eye (e.g., optically, geometrically, etc.), is often based on the assumption that the eye is maintained in a defined position and orientation with respect to the diagnostic device. The patient may be positioned by a human operator of the ophthalmic device and instructed, for example, to look into the device at a target object (e.g., a fixation light) to align the patient's line-of-sight (e.g., the axis along which a person looks at things) to an optical axis of the ophthalmic device. If the patient isn't properly fixated, readings may be inaccurate and/or the system may not be able to properly function.

To ensure accurate data acquisition, the human operator of the ophthalmic device is often tasked with monitoring the patient, leading the patient through an initialization procedure, and/or monitoring feedback from the device during data acquisition to determine whether the patient has been properly fixating on a target object to align the eye. One known technique includes relying on the cooperation of the patient to fixate on a target object as instructed by a device operator. However, existing approaches have many drawbacks including human error in the patient's attempt to fixate (e.g., an elderly patient may be unable to maintain eye position, a patient may lack sufficient concentration to fixate the eye, the patient may not look directly at the target object, etc.) and human error and variability by the operators monitoring the patient during the procedure. In another approach, retina scanning and imaging analysis may be used to track the patient's eye position and orientation, but operation of a retinal imaging system can interfere with a diagnostic procedure. As a result, retina scanning and imaging systems are often shut down or otherwise rendered inoperable for use in eye tracking during a diagnostic procedure performed using the ophthalmic device.

Other drawbacks of conventional systems include that the patient may not know when the measurement starts and may lose fixation, blink or move in other ways that impact the reliability of the measurement. The patient may be asked to fixate for a long period of time, which may be uncomfortable for the patient and lead to the eye being in a sub-optimal state. The operator may also be tasked with determining an optimal condition of the eye for taking the measurement. For example, the eye may dry over the course of a measurement procedure and moisture may get renewed each time a patient blinks, leading to constant changes in the reflectivity of the eye.

In view of the foregoing, there is a continued need in the art for improved techniques for determining and/or tracking the position, orientation and condition of a patient's eye during an ophthalmic procedure.

SUMMARY

The present disclosure relates generally to systems and methods that includes patient control of eye diagnostic data acquisition. The systems and methods provided herein may be used to determine an optimal time when the eye is ready for measurement.

In one or more embodiments, a system includes an ophthalmic device configured to measure characteristics of an eye, an eye tracker configured to capture a first stream of images of the eye, and a logic device configured to analyze the first stream of images to determine whether the eye is fixating on a target object, detect a predetermined blink sequence in the first stream of images, start a stable tear film interval after a predetermined tear stabilization period, and during the stable tear film interval, capture at least one measurement of the eye using the ophthalmic device when the eye is fixating on the target object. The blink sequence may include a plurality of blinks in succession and the detection of the blink sequence may include processing the images through neural network trained to detect an open eye and/or a closed eye.

In some embodiments, the eye tracker is configured to capture a first image of the eye from a first location and a second image of the eye from a second location, and the logic device is further configured to detect a first plurality of eye characteristics from the first image, the eye characteristics having first corresponding image coordinates, detect a second plurality of eye characteristics from the second image, the eye characteristics having second corresponding image coordinates, and determine a calibration offset and a calibration gain based at least in part on the first corresponding image coordinates, the second corresponding image coordinates, the first location and the second location. The logic device may be further configured to determine an eye fixation position and orientation relative to an optical axis of the eye tracker based at least in part on the first corresponding image coordinates and/or the second corresponding image coordinates.

In some embodiments, the logic device is configured to estimate eye fixation parameters based at least in part on the determined eye fixation position and orientation, receive the first stream of images from the eye tracker, and track a current eye position and orientation by analyzing at least one image from the first stream of images to determine the current eye position and orientation relative to the eye fixation parameters, wherein the eye fixation parameters comprise a reference position and orientation of the eye when fixated.

The logic device may be further configured to determine the fixation position relative to the optical axis of the eye tracker by constructing and analyzing a histogram of detected eye positions and orientations, wherein analyzing the histogram further comprises determining whether coordinates of a relative maximum value comprise a fixation position and orientation, and wherein determining whether coordinates of the relative maximum value comprise a fixation position and orientation further comprise comparing the relative maximum value with a threshold and/or an average coordinate value of the histogram.

In some embodiments, the system further comprises a retina imaging system comprising an optical coherence tomography (OCT) scanner configured to perform a retinal scan, wherein the eye tracker is further configured to capture a stream of images of the eye during the retinal scan, wherein the retina imaging system is further configured to capture a plurality of retinal images of the eye, detect whether a fovea is present in one or more of the plurality of retinal images of the eye, and identify a first retinal image from the plurality of retinal images of the eye having the detected fovea, and wherein the logic device is further configured to determine a corresponding image from the stream of images having a temporal proximity to the first retinal image, and analyze the corresponding image to determine eye fixation parameters.

In some embodiments, the logic device is configured to track the eye position and orientation and calculate an offset from the eye fixation parameters and determine if the offset is less than a threshold value, wherein when the offset is less than the threshold value the eye is determined to be fixated and the control processor generates an indication of fixation, and wherein when the offset is greater than the threshold value the eye is determined to be out of alignment and the control processor generates an indication of no fixation.

The logic device may be further configured to perform an eye diagnostic procedure and track eye position using the eye tracker during the eye diagnostic procedure. The system may further include a diagnostic device configured to perform an eye diagnostic procedure while tracking a position and orientation of the eye using the eye tracker, wherein the diagnostic device is configured to modify the eye diagnostic procedure based, at least in part, on data representative of eye fixation parameters and a tracked eye position.

In various embodiments, a method includes capturing, using an eye tracker, a first stream of images of the eye, analyzing the first stream of images to determine whether the eye is fixating on a target object, detecting a predetermined blink sequence in the first stream of images, tracking a stable tear film interval after the predetermined tear stabilization period, and during the stable tear film interval, capturing at least one measurement of the eye using an ophthalmic device when the eye is fixating on the target object. The blink sequence may include a plurality of blinks in succession and detecting the predetermined blink sequence in the first stream of images may comprise processing the images through neural network trained to detect an open eye and/or a closed eye.

The method may further include capturing a first image of an eye from a first location, capturing a second image of the eye from a second location that is different than the first location, detecting a first plurality of eye characteristics from the first image, the eye characteristics having first corresponding image coordinates, detecting a second plurality of eye characteristics from the second image, the eye characteristics having second corresponding image coordinates, and determining a calibration offset and a calibration gain based at least in part on the first corresponding image coordinates, the second corresponding image coordinates, the first location and the second location.

The method may further include capturing a stream of images of the eye, detecting an eye position and orientation in the stream of images based at least in part on coordinates of the detected eye characteristics, the calibration offset and the calibration gain, and determining an eye fixation position and orientation relative to an optical axis. The method may further include estimating eye fixation parameters based, at least in part, on the determined eye fixation position and orientation, and tracking the eye position and orientation by analyzing one or more images from the stream of images to determine the eye position and orientation relative to the eye fixation parameters, wherein the eye fixation parameters comprise a reference position and orientation of the eye when fixated. The method may further include training a neural network to receive the stream of images and output a determination of an eye position and/or tear film status.

In some embodiment, the method further includes detecting the fixation position relative to the optical axis by constructing and analyzing a histogram of detected eye positions and orientations, wherein analyzing the histogram further comprises determining a relative maximum value.

The method may further include performing a retina imaging scan of the eye using an optical coherence tomography (OCT) scanner, capturing a plurality of retinal images of an eye from the retina imaging scan, capturing a stream of images using an imaging device configured to image a surface of the eye, detecting whether a fovea is present in one or more of the plurality of retinal images, identifying a first retinal image from the plurality of retinal images having the detected fovea, determining a corresponding image from the stream of images having a temporal proximity to the first retinal image, and analyzing the corresponding image to determine eye fixation parameters.

In some embodiments, the method further includes tracking an eye position and orientation and calculating an offset from the eye fixation parameters and determine if the offset is less than a threshold value, wherein when the offset is less than the threshold value the eye is determined to be fixated and the control processor generates an indication of fixation, and wherein when the offset is greater than the threshold value the eye is determined to be out of alignment and the control processor generates an indication of no fixation.

The method may further include performing an eye diagnostic procedure while tracking the position and orientation of the eye using an image capture device, and modifying the eye diagnostic procedure based, at least in part, on data representative of eye fixation parameters and a tracked eye position.

The scope of the present disclosure is defined by the claims, which are incorporated into this section by reference. A more complete understanding will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Aspects of the disclosure and their advantages can be better understood with reference to the following drawings and the detailed description that follows. It should be appreciated that like reference numerals are used to identify like elements illustrated in one or more of the figures, where showings therein are for purposes of illustrating embodiments of the present disclosure and not for purposes of limiting the same. The components in the drawings are not necessarily to scale, emphasis instead being placed upon clearly illustrating the principles of the present disclosure.

DETAILED DESCRIPTION

Figure 1A:
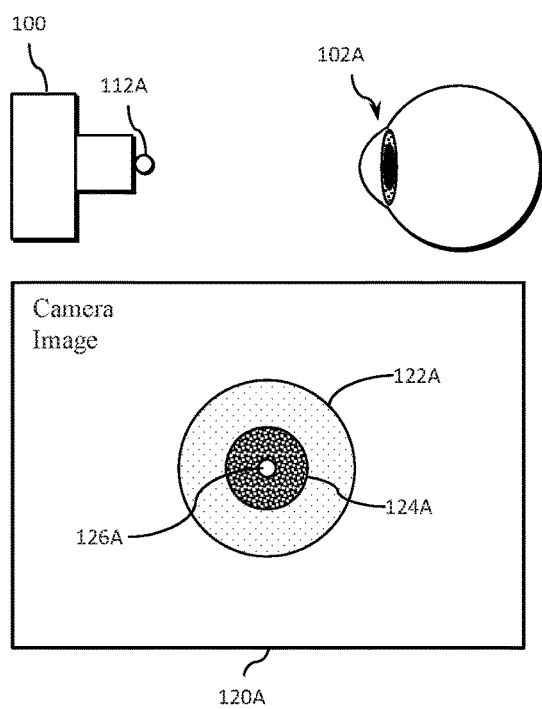
FIGS. 1A and 1B illustrate an example eye tracking and imaging system, in accordance with one or more embodiments of the present disclosure.

The present disclosure provides systems and methods for tracking the position, orientation and/or condition of an eye during an ophthalmic procedure.

In order to obtain high quality diagnostic data for an ophthalmic diagnosis, the eye should be in a well-defined position and condition during measurement. For example, for many ophthalmic devices a measurement sequence is conducted when the patient's eye is fixating along an optical axis of a target device (e.g., along the axis and/or offset within a range of error acceptable for the measurement), and the patient's eye has an intact tear film. In various embodiments, improved systems and methods include automated calibration of an eye tracking device, accurate eye position and fixation determinations, improved eye tracking procedures, absolute fixation position and estimated absolute fixation position determinations, and improve timing of measurement data acquisition based on fixation status and/or tear film status.

An intact tear film is often a prerequisite for a reflection-based diagnostic device like keratometers or topographers, which operate using reflections from the cornea surface. In many applications, dry areas of the cornea do not allow for an optimal reflection-based measurement. The tear film is also a refractive surface that may be used by certain diagnostic devices, such as a wavefront measuring device. The tear film may be restored each time the patient blinks as the eye lid distributes the tear liquid over the eye. The tear film will stabilize after t1 seconds (e.g., 0.5-2 second), stay intact for t2 seconds (e.g., 1-3 seconds) and then dry out until the next blink. These durations (t1 & t2) may vary from patient to patient and may be estimated for a patient pool through clinical studies, for example.

In addition to an intact tear film, stable fixation of the eye ensures the visual axis of the patient is aligned with the optical axis of a diagnostic device. If the patient is not fixating or fixating poorly the consequences may include inaccurate measurements, unreliable measurements, or inability of the device to perform the measurements, etc. Fixating on a static fixation target for long time can be challenging for the patient. The time in which a patient is able to fixate accurately also varies from patient to patient. In various embodiments disclosed herein, systems and methods track the position and orientation of the eye (e.g., whether the eye is properly fixating) and the condition of the eye (e.g., whether the tear film is intact) to identify intervals of time during which accurate and reliable measurements may be taken.

In some ophthalmic systems, the quality of the acquired data may depend on the skills and awareness of the operator. In these systems, the operator may determine when the position, orientation and condition of the eye are appropriate for measurement, resulting in variability in measurements taken by different operators. For systems that use automated measurement, the measurements may occur independent of the whether the patient is ready for the measurement, which may lead to acquisition when the patient is not fixating and/or the tear film is not stable (e.g., outside of t2). The patient may also be required to fixate during a long measurement sequence not knowing the exact point in time when the measurement starts. For example, in one approach, an operator may position the patient to align the patient's eye with an optical axis of the diagnostic system. The patient may be instructed to fixate on a known target point to align the patient's gaze until the operator and device are ready for the measurement.

After the patient is determined to be fixating, the operator may instruct the patient to blink to establish a tear film. The patient then tries to maintain fixating on the target point during the procedure. The operator and/or device may then capture a measurement of the patient's eye. However, the measurement may be captured before the tear film stabilizes (e.g., during time period t1), during the period in which the tear film has stabilized (during time period t2), or after the tear film starts to degrade. Thus, the captured measurement occurs during an unknown tear film state, leading to unreliable measurements. The improvements of the present disclosure allow for data acquisition when the tear film is stabilized, thereby improving diagnostic accuracy. In some embodiments, the improved system may function independent of the operator and the time required for the patient to fixate is reduced.

The systems and methods disclosed herein further include improved initialization and calibration of ophthalmic systems to a patient's own eyes, improved eye tracking, improved absolute fixation position and orientation determination, and other improvements and advantages over conventional systems. The improved initialization and calibration techniques disclosed herein allow for more accurate measurement of a patient's eye and may be used in diagnostic systems that determine whether the patient's line-of-sight (also referred to herein as the patient's visual axis) is in alignment with an optical axis of the diagnostic system. The patient's line-of-sight/visual axis may be the axis along which the patient's eye is oriented to look at an object. The systems and methods disclosed herein allow for simpler, shorter and more accurate system initialization and calibration and more accurate fixation determinations. The diagnostic data acquired in accordance with the systems and methods disclosed herein is more meaningful and accurate than data acquired through conventional approaches. If the patient is not properly fixating during the measurement and this is not accounted for, the accuracy of the readings may suffer significantly. For many implementations, the accuracy with which a person can fixate (actively control the gaze on a static target) may be in the order of 1 degree but may be significantly worse than that depending on the condition of the eye (e.g., strong cataract). Systems and methods disclosed herein improve accuracy by determining and using a gaze profile of the patient's eye during the measurement. Use of the patient's gaze profile can eliminate measurement noise in the readings introduced by eye gaze motion and inability to steadily fixate.

Figure 1B:
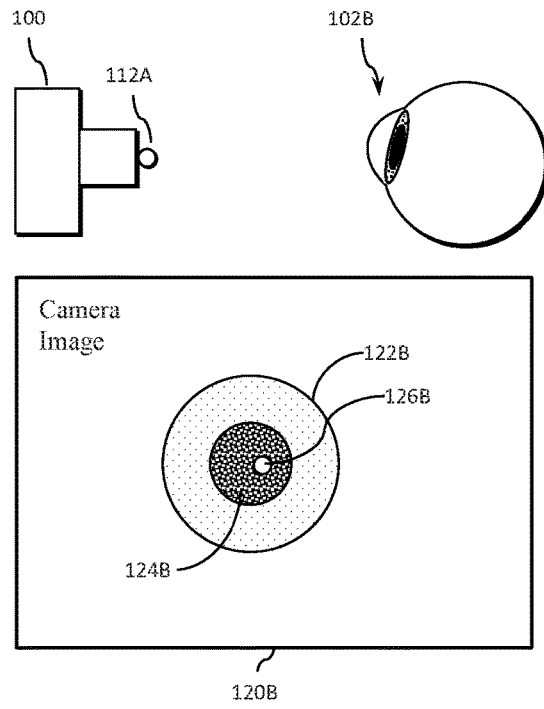

Referring to FIGS. 1A and 1B, an example eye tracking system for use with an ophthalmic device will now be described in accordance with one or more embodiments. One way to track eye gaze is by analyzing a camera image to compare the position of the pupil in the image to the position of a corneal reflection created from an illumination source that is fixed in space relative to the observing camera. The system illustrated in FIGS. 1A and 1B includes a calibration procedure in which the patient is instructed to fixate on known fixation points that allow the system to calibrate the specifics of the observed eye. As illustrated, an eye tracking system 100 includes image capture components (e.g., a visible light camera) and an illumination source 112A (e.g., one or more light-emitting diodes (LEDs)) that is in a known fixed position relative to the image capture components. The eye tracking system 100 is configured to image and track an eye 102A by capturing and analyzing a stream of images of the eye 102A, such as example camera image 120A.

The camera image 120A is analyzed to identify one or more characteristics of the eye 102A, such as an image of a cornea 122A, a pupil 124A and a reflection 126A of the illumination source 112A. By identifying one or more eye characteristics in the camera image 120A, information about the position and orientation of the eye 102A, such as the eye gaze azimuth GA and the eye gaze elevation GE, may be determined. The camera image 120A may be analyzed to determine coordinates of alignment and/or offset positions of the eye during a procedure. For example, the camera image 120A may be analyzed to determine the image coordinates [CRx, CRy] of the corneal reflection 126A (CR) of the illumination and/or the image coordinates [PCx, PCy] of the pupil 124A (e.g., the center of the pupil PC).

The image coordinate differences between the corneal reflection CR and the pupil center PC may be calculated as follows:

$$Dx = CRx - PCx$$

$$Dy = CRy - PCy$$

These image coordinate differences are proportional to the azimuth (GA) and elevation (GE) of the eye gaze:

$$Dx \sim GA$$

$$Dy \sim GE$$

To more accurately derive the eye gaze azimuth GA and the eye gaze elevation GE from Dx and Dy, an offset (ax, ay) and a gain (bx, by) in may be applied to each image coordinate x and y, respectively:

$$GA = ax + bx \cdot Dx$$

$$GE = ay + by \cdot Dy$$

The variables a and b may depend on a variety of factors, including the anatomy of the specific eye being imaged, the setup of camera and illumination source and the optics of the camera, for example. In some embodiments, the determination of a and b may include an initialization procedure during which the patient to be tracked is asked to fixate on a set of targets that stimulate a defined gaze in the eye (e.g., a grid of fixation points). For example, FIG. 1A illustrates a scenario where the patient is asked to focus at a first known fixation point, such as a point proximate to or aligned with the optical axis of the eye tracking system 100. FIG. 1B illustrates a scenario in which the eye 102B is observing a second known fixation point, such as a point next to the camera. The camera image 120B may include an image of a cornea 122B, a pupil 124B and a reflection 126B of the illumination source 112A. Because the camera position and orientation, eye position and orientation, and the location of the fixation points are known during fixation, the eye gaze azimuth GA and eye gaze elevation GE may be known or estimated for each fixation point. The two camera images 120A and 120B, respectively, are analyzed to determine the coordinates, x and y, of one or more eye characteristics in each image (e.g., center of pupil in the image, location of reflection in image). The system of equations may then be solved for a and b initialize and calibrate the system for eye tracking.

The initialization procedure described with reference to FIGS. 1A and 1B may be cumbersome to implement and/or prone to error for some patients. The patient may be instructed, for example, to separately fixate on a grid of 5 or more fixation points to calculate the values of a and b by a statistical or other mathematical analysis (e.g., a least squares analysis). Asking the patient to fixate on a number of targets requires significant patient cooperation and the patient's gaze directed to any one point is subject to error.

Figure 2:
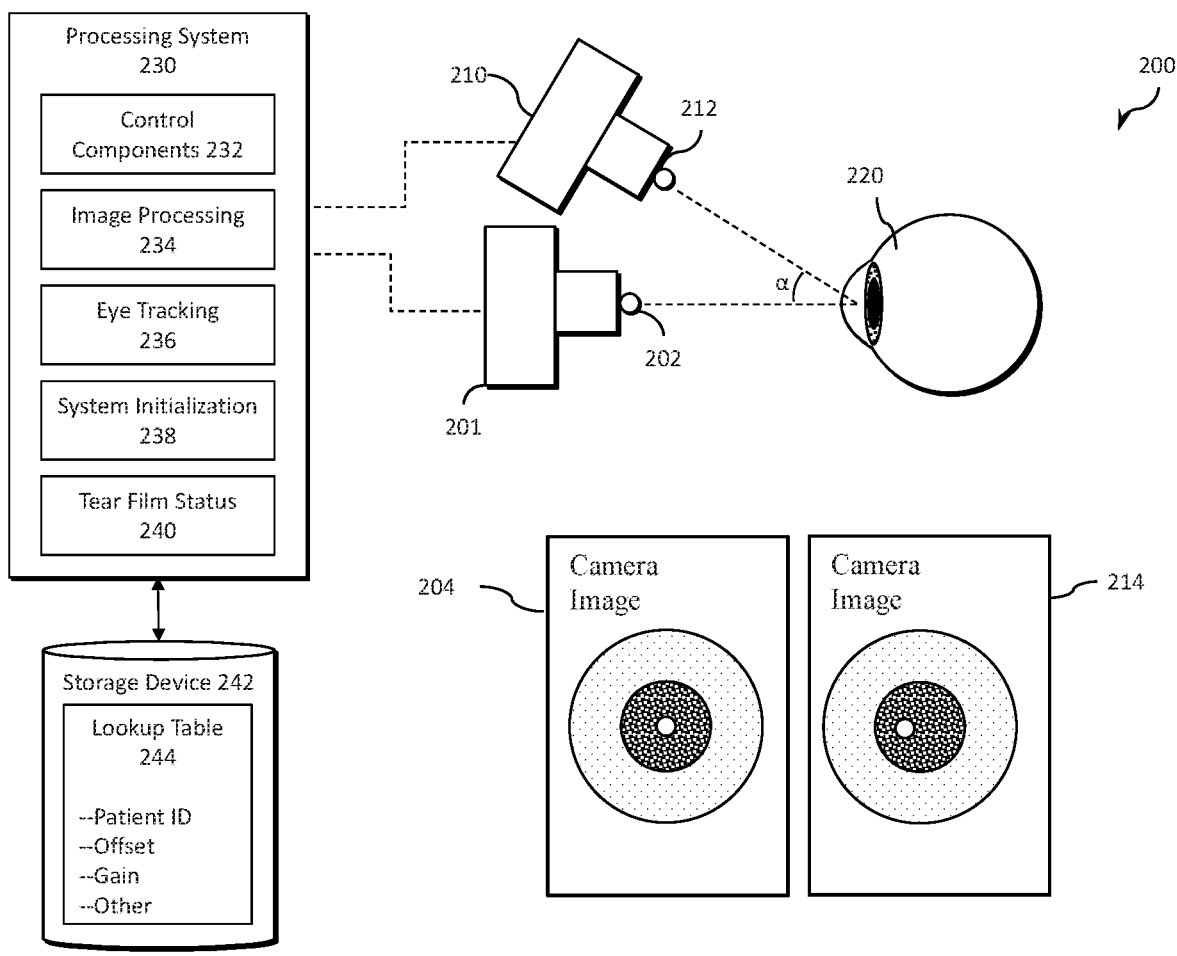
FIG. 2 illustrates an example eye tracking and imaging system with automatic initialization and calibration, in accordance with one or more embodiments of the present disclosure.

Further embodiments of the present disclosure will now be described with reference to FIG. 2. FIG. 2 illustrates an eye tracking system 200 that includes automated initialization and calibration components and procedures that allow for accurate eye gaze tracking in diagnostic systems for keratometry, corneal topography, aberrometry and other uses. Although the systems and methods illustrated in FIG. 2 may be fully automated and reduce/eliminate the need for the patient to run through a cumbersome initialization procedure, various aspects may be used with manual and/or other automatic eye tracking initialization and calibration procedures, including procedures that include an operator guiding a patient to fixate on a series of known fixation points.

The eye tracking system 200 may be implemented in any device that uses accurate fixation of the eye. For example, many ophthalmic devices such as keratometers, topographers and aberrometers rely on accurate eye fixation during diagnostic procedures. Having accurate information about the actual eye gaze during acquisition of diagnostic data may allow for filtering out of readings with poor fixation, compensating the readings with poor fixation by accounting for the actual gaze orientation, and/or more accurate comparison of diagnostic readings (e.g., corneal topography maps) taken at different points in time and accounting for the gaze difference when comparing the readings.

The eye tracking system 200 includes a first image capture device 201 having a first illumination source 202 and a second image capture device 210 having a second illumination source 212. The first image capture device 201 and first illumination source 202 may be configured, for example, as a single camera eye tracker adapted to capture images of the patient's eye 220. The first image capture device 201 may include visible spectrum image capture components arranged to capture an image of the surface of the patient's eye 220 along an optical axis of an ophthalmic device. The second image capture device 210 may include visible spectrum image capture components arranged to capture an image of the surface of the patient's eye 220 from a known angle α (e.g., 20-degrees above the first image capture device 210). In some embodiments, the second image capture device 210 is the same type of imaging device as the first image capture device 210 (e.g., comprised of the same or similar components, same device model number, etc.) and disposed at approximately the same distance from the eye 220 to generate a second camera image 214 having similar image characteristics as the first camera image 204.

A processing system 230 controls the operation of the eye tracking system 200 and may include control components 232, imaging processing components 234, eye tracking components 236 and system initialization components 238. The processing system 230 may include one or more systems or devices implemented through a combination of hardware, firmware, and/or software. In some embodiments, the control components 232 are configured to manage the operation of the first image capture device 201 and the second image capture device 210, including providing instructions to synchronize image capture operations of the image capture devices 201 and 210. Depending on the system configuration, the first image capture device 201 and second image capture device 210 may be instructed to capture images at the same time and/or sequentially with a short interval between images (e.g., timed to capture two images of the eye 220 in the same position). The image processing components 234 are configured to analyze the captured images to determine one or more eye characteristic, such as a center of a pupil, location of cornea and/or location of reflection in the image. The eye tracking components 236 are configured to track an eye position based on a calibrated measurement of the eye characteristics identified in the one or more image.

The system initialization components 238 are configured to initialize the measurement equations to accurately calculate the eye gaze azimuth GA and the eye gaze elevation GE from the captured image data. In various embodiments, a patient is instructed to fixate on a known fixation point approximating an optical axis of the diagnostic device. The operator may interact with the eye tracking system 200 using a user interface to initiate the eye tracking procedure and guide the user through the initialization processing. In some embodiments, images are captured from each of the image capture devices 201 and 210 and when the patient is fixating on the known point. A first camera image 204 captured by the first image capture device 201 and a second camera image 214 captured by the second image capture device 210 are used in the system initialization routine. The eye fixation may be determined, for example, based on the judgment of the operator, using a retina imaging system to detect the fovea, through image analysis of the location of the reflection relative to the center of the pupil, through a statistic analysis of multiple images captured over time, and/or through other techniques.

The two images, 204 and 214, are processed through image processing components 234 to determine eye characteristics for each image. The two sets of eye characteristics represent two different measurements taken when the eye 220 was fixating at a known fixation point. The two sets of equations may then be used to solve for the calibration offset a and gain b, which are used to determine the eye gaze azimuth GA and the eye gaze elevation GE from the image data. By using a second camera to image the eye from a second angle, two images and measurements of the eye may be taken for a single fixation point, allowing the offset and gain to be determined without a cumbersome, multi-fixation point initialization procedure. In other embodiments, one or more additional cameras may be provided at other angles and/or more than one fixation point may be used as necessary to further minimize error.

The calibration offset and gain may be used in a process that determines an eye position and orientation based on captured images. In some embodiments, the calibration offset and gain may be immediately available for use by the eye tracking system 200. In some embodiments, the calibration offset and gain are stored in a storage device 242 (e.g., random-access memory, hard drive, flash memory, cloud storage, etc.) in a database or lookup table 244. For example, the lookup table may store a patient identifier and the calibration offset and gain values associated with the patient's eye. Other information may also be stored, such as the camera type, camera positions, and date of measurement. In operation, the eye tracking system 200 may use the lookup table to determine an absolute orientation of the eye from pixel positions of the pupil center and corneal reflections as measured from images acquired by the eye tracker 200.

The processing system 230 may also include a tear film status component 240 configured to analyze captured images to detect eye open and eye close events, and track the status of the tear film, including whether the patient recently blinked, whether the tear film is stabilized for measurement and/or whether the eye is drying and the tear film needs to be renewed. Along with the calibration and initialization processes and absolute eye position determination and fixation tracking disclosed herein, the use of the tear film status allows for more accurate eye diagnostics.

Figure 3:
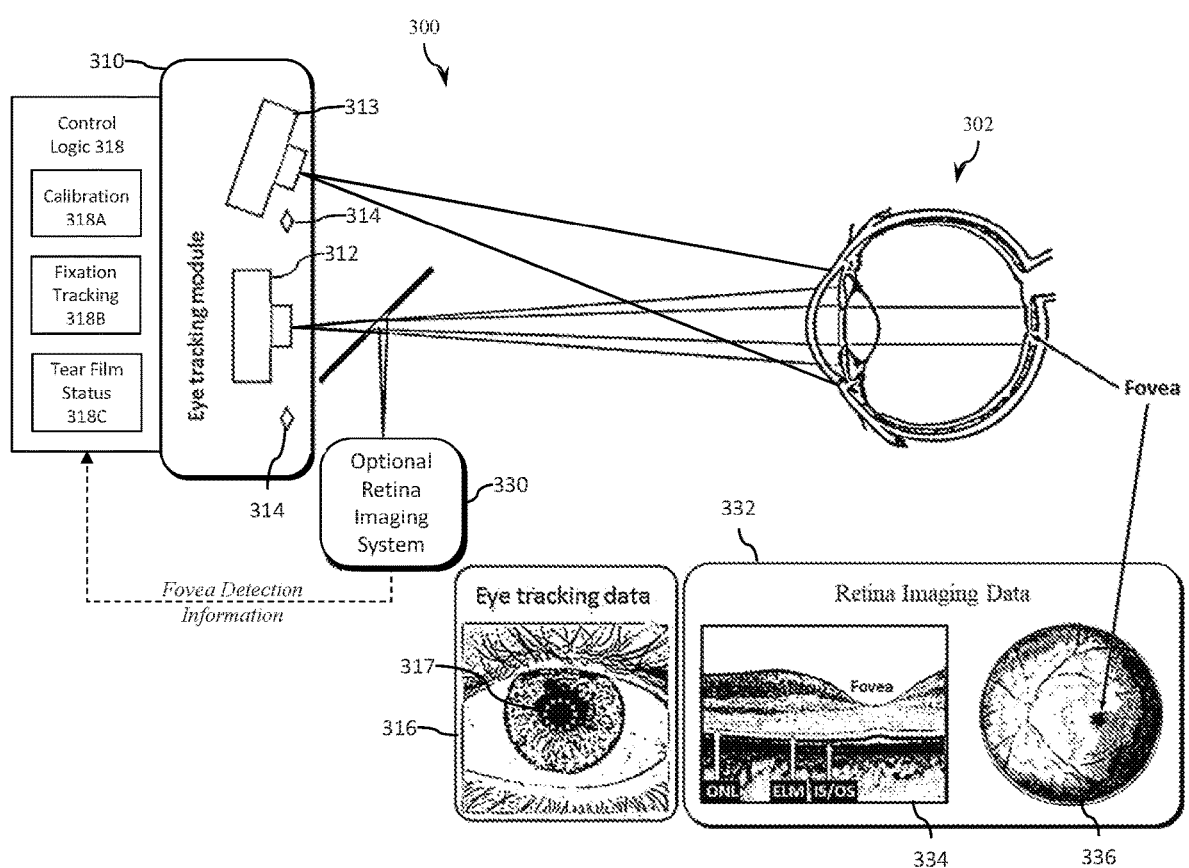
FIG. 3 illustrates an example eye tracking and imaging system, in accordance with one or more embodiments of the present disclosure.

Various example embodiments of the present disclosure will now be described in further detail with reference to FIGS. 3-11. Referring to FIG. 3, a system 300 in accordance with one or more embodiments includes an eye tracking module 310 (also referred to herein as an "eye tracker") and an optional retina imaging system 330, which are communicably coupled. The eye tracking module 310 is configured to track the orientation of an eye 302 and may include a first imaging device 312, second imaging device 313 and one or more illumination components 314. In some embodiments, the first imaging device 312 and second imaging device 313 are digital cameras or other digital imaging devices configured to image certain features of the eye such as the pupil and corneal limbus (the border between the cornea and the white of the eye, i.e., the sclera) and reflections from one or more of the illumination components 314. In some embodiments, for example, the illumination components 314 may comprise a light emitting diode (LED) ring positioned around the camera optics (e.g., coaxial illumination around the imaging device) such that the center of the ring resembles the center of curvature of the cornea.

The system 300 includes control logic 318, which may include a logic device such as a processor executing stored program instructions configured to perform the functions disclosed herein. In some embodiments, the control logic 318 performs a measurement sequence with a plurality of images captured by the first imaging device 312. The measurement sequence determines the position and orientation of the eye 302 by using the position of detectable features of the eye 302 in the image data (such as eye tracking data 316), such as the pupil, limbus, and iris features. The measurement sequence may also determine the position of the reflection of the illumination system at the cornea (such as the reflections 317 comprising a circle pattern of illuminated elements). In some embodiments, during the measurement sequence, the position and orientation of the eye 302 is continually determined using the captured images. The control logic 318 may also perform an initialization and calibration component 318A (e.g., the sequence described with reference to FIG. 2) including calculating a calibration offset and gain from a pair of images captured from the imaging devices 312 and 313, respectively, for the patient's eye 302. The calibration offset and gain may be used to accurately calculate the absolute eye position and orientation from pixel positions of eye characteristics identified in captured image data.

The control logic 318 may further include fixation tracking components 318B configured to track whether the eye 302 is properly fixating and/or an offset from a fixation position, and tear film status components 318C configured to detect and track the status of the tear film on the eye 302. Eye measurements may be conducted based on the fixation status and/or tear film status. For example, the tear film status components 318C may include a procedure to help maintain an intact tear film during measurement. In various embodiments, the patient may be instructed to blink or otherwise open and close the eye 302 to provide moisture to the eye 302. The tear film status components 318C may detect the eye closing and reopening and track the time until and through tear film stabilization. When the tear film is no long stabilized for measurement (e.g., the eye is drying) the patient may be instructed to blink again to repeat the process.

The control logic 318 may be embodied in the eye tracking module 310, the retina imaging system 330 and/or in other system components. The control logic 318 is configured to detect relative eye movement during operation of the eye tracking module 310, which may include detecting and tracking eye features (e.g., detect the pupil) from the captured images and knowledge of the illumination source position. For example, detecting and calculating an offset of the center of the pupil and an offset of the cornea curvature may provide information about the relative gaze of the eye.

The optional retina imaging system 330 may include any device or system for imaging the retina of the eye 302. The retina imaging system 330 may be implemented as a retina optical coherence tomography (OCT) system, a retina optical system, or similar system for imaging the retina. In some embodiments, the retina imaging system 330 and/or the control logic 318 is configured to detect the fovea of the patient at least once during the full measurement sequence. As a result, the retina imaging system 330 does not need to be active during the full diagnostic sequence (e.g., for technical or safety reasons) and may be shut down or paused as desired.

If the patient is fixating, then the fovea will be present in the retina imaging data. The fovea often appears as depression in the retina which may be detected in certain retina imaging systems. In various embodiments, the retina imaging system 330 generates retina imaging data 332, such as a retina OCT image 334 and/or a fundus image 336. The retina imaging system 330 may comprise retina OCT scanning system, a fundus imaging system, or other similar device. If the patient is fixating on a target object associated with the system 300, the fovea will be present in the center of the optical axis of the retinal imaging device. The retina imaging device may only need to scan the center part around the optical axis of the device. In some embodiments, the retina imaging device is configured to image the back of the eye for fovea detection. If the system needs to image a different part of the eye (e.g., high resolution scan of the cornea), then the fovea will not be visible in the image and the eye tracking module 310 will be used to track the eye position and rotation.

The system 300 coordinates the processing of information relating to the orientation of the eye from the imaging devices 312 and 313 of eye tracking module 310 (such as eye tracking data 316, including detected illumination source reflections 317, captured from each image capture component). The system 300 may further coordinate the eye tracking data 316 with the information from the optional retina imaging system 330 (such as retina imaging data 332). In operation, if the system 300 (e.g., via the retina imaging system 330 and/or control logic 318) detects the fovea in a certain area of the retina imaging data 332, then the corresponding orientation of the eye is known to the system 300. With this information, the system 300 may further determine if the patient is fixating correctly even in phases of the measurement in which retina imaging is not available. The fixation information may be used by the eye tracking module 310 to identify images (e.g., images of the eye when fixating) for used in an initialization and calibration process. The calibrated eye tracking module 310 may then be used to accurately calculate the absolute eye position and orientation from the captured images.

The eye tracking module 310 may be configured to image and the track eye position and eye rotation at the same time as the retinal imaging. In some embodiments, the captured images include associated temporal characteristics such as a timestamp, frame reference (e.g., 10 frames ago), or other information allowing synchronization of the retinal images and the images captured from the first imaging device 312 and the second imaging device 313. After the fovea is detected, the fovea detection information, which may include a corresponding temporal characteristic and an indication of whether the fovea was detected may be provided to control logic 318, eye tracking module 310, and/or other system components.

In some embodiments, the analysis of the position and orientation of the eye 302 includes a method that compares the orientation/position of the eye at the time the fovea was visible with the retina imaging system with current eye tracking data. The system 300 may be used, for example, in a diagnostic procedure that includes a measurement sequence. By tracking the eye position and orientation during a procedure using the eye tracking module 310, measurement data may be gathered and analyzed with the corresponding eye tracking data. In one embodiment, measurement data acquired when the eye 302 was fixated (e.g., when the eye position is within an acceptable offset from a fixation position) is considered valid and used for further diagnostics/analysis and measurement data acquired when the eye 302 was not fixated (e.g., when the eye position is outside an acceptable offset from a fixation position) may be ignored and/or discarded.

In various embodiments, the system 300 uses the fovea detection information to establish reference fixation information, which may include a certain orientation of the pupil in relation to the cornea. The eye tracking module 310 can receive fovea detection information (e.g., fixation determined at particular time or other temporal reference), retrieve one or more corresponding images from the same timeframe, and analyze the captured image(s) to determine the specific relationship between the pupil and the cornea center during fixation. The system may be initialized and calibrated using the captured images to determine a calibration offset and gain for more accurate measurement results. The eye position may then be tracked by comparing the eye position and orientation in newly captured images with the eye position and orientation from reference images. This allows the retina imaging system 330 to image another part of the eye 302 (or operation of other ophthalmic equipment as desired) while the eye tracking module 310 confirms that the eye is fixating. The eye tracking module 310 may provide fixation information to the retina imaging system 330 indicating whether a current scan was taken while the eye was fixating (within a range of error relative to the reference data) or whether the current scan was taken while the was not fixating, such as when the offset between the current eye position and the reference eye position exceeds a threshold value.

During operation of the system 300 the retina imaging system 330 may be shut down during a diagnostic or other procedure such that retina imaging data 332 is no longer generated. If the fovea has been previously detected by the retina imaging system 330 at least one time, the system 300 can continue to provide the device operator information about the patient's eye fixation, even during phases of the procedure in which no retina imaging is available. For example, the system 300 may compare the current eye position and orientation captured using the eye tracking module 310 to the eye position and orientation determined when the retina imaging system 330 detected the fovea. The eye tracking module 310 may provide an indication to the device operator through one or more visual (e.g., indicator light, status information on a display screen) or audible cues (e.g., beeps). The eye tracking module 310 may further provide fixation information to other components of the system 300, for example, to control operations that require eye fixation and/or to validate/invalidate acquired data. It will be appreciated that the systems and methods described in FIG. 3 are example implementations of various embodiments, and the teachings of the present disclosure may be used in other eye tracking systems, such as systems or devices using an illumination system generating purkinje reflections and a camera to capture digital images of the eye.

To aid in determining whether the eye is fixated, the control logic 318 may be configured to determine a current position and orientation of the eye and calculate an offset to determine whether the eye is sufficiently fixated on the desired object. In one embodiment, one or more thresholds may be determined and any offset lower than a corresponding threshold will result in a determination that the eye is fixated. In some embodiments, the fixation determination and threshold are application dependent and different offsets may be acceptable for difference implementations.

In some embodiments, the retina imaging system 330 identifies a timeframe (e.g., a period of time, one or more images, a sequential index value, etc.) in which the fovea was detected, allowing the eye tracker to identify corresponding eye tracking imagery that was taken at the same, or approximately the same time. The eye tracking module 310 and/or control logic 318 may then perform an initialization and calibration procedure to determine a calibration offset and gain which may be used to accurately calculate the eye position and orientation from the captured images. The eye tracking module 310 may then determine a reference position of the eye associated with the fixation position, including relative position of the pupil and cornea. The eye fixation information may be immediately used by the system 300 to track the eye position and orientation and/or stored and retrieved for use by the system 300 at a later time. For example, eye fixation information may be determined and stored for a patient and retrieved for use by the system 300 (or similar system) for subsequent procedures for the patient or for offline analysis of captured images.

While the retina imaging system 330 is performing other scans and/or other ophthalmic components are in operation, the eye tracking module 310 captures a stream of images and analyzes the eye position and alignment with reference to the position and orientation determined from the reference image(s). This analysis may be performed in real time during a procedure and/or offline (e.g., when analyzing previously captured data). The current images are compared to the reference image(s) and an offset is calculated. If the offset is less than a threshold then the eye is fixating and the corresponding retina images are accurate. If the offset is greater than the threshold then the eye is not fixating and the corresponding retina images may be flagged, discarded or other action taken. The images may further be synchronized with other information, including tear film status, which may be stored with a temporal reference allowing for later synchronization and processing with stored images.

In some embodiments, the eye tracking module 310 continually images the eye throughout the procedure. For each frame, the pupil position may be detected in the image based, at least in part, on where reflections are detected in the image stream. In various embodiments, the information tracked and recorded may include one or more of the image, image features extracted from the image, image properties, pupil location and/or reflection position in the image. The eye tracking system and retina imaging system are synchronized such that for each retina scanned image, one or more corresponding eye tracker images may be identified. In one embodiment, there is a one-to-one correspondence. In other embodiments, the images are synchronized through a timestamp or other synchronization data associated with the captured images.

It will be appreciated that while the eye tracking module 310 and optional retina imaging system 330 are described as separate components, the system 300 may comprise a diagnostic device with various subcomponents including the eye tracking module 310, the retina imaging system 330 and other subcomponents. In some embodiments, a central processor may be provided to control the operation of the system 300, synchronize and control communications between the two systems and perform other system functions. Analysis of the eye position and orientation may be performed in real-time by the system 300, or later after the procedure is complete. Online, the system 300 may provide feedback to the patient and operator. Offline, the system 300 and/or other systems may perform more a complex analysis to achieve more accurate scans and results.

In some embodiments, the system 300 may comprise a larger diagnostic device that includes two or more cameras (e.g., for imaging the surface of the eye), and a second component for measuring the retina. The system 300 may include a plurality of sensors configured to image the eye to create a 3-D eye model. A first sensor system may include two or more cameras to recover the cornea shape and do the eye tracking. A second sensor system may include a wavefront sensor that measures the wavefront of the eye (optical parameters of the eye). A third sensor may include an OCT system that can measure distances between different refractive surfaces of the eye. The OCT may include multiple modes and resolutions including a full eye mode, half-eye mode (front of eye) and cornea mode (having higher resolution).

Figure 5:
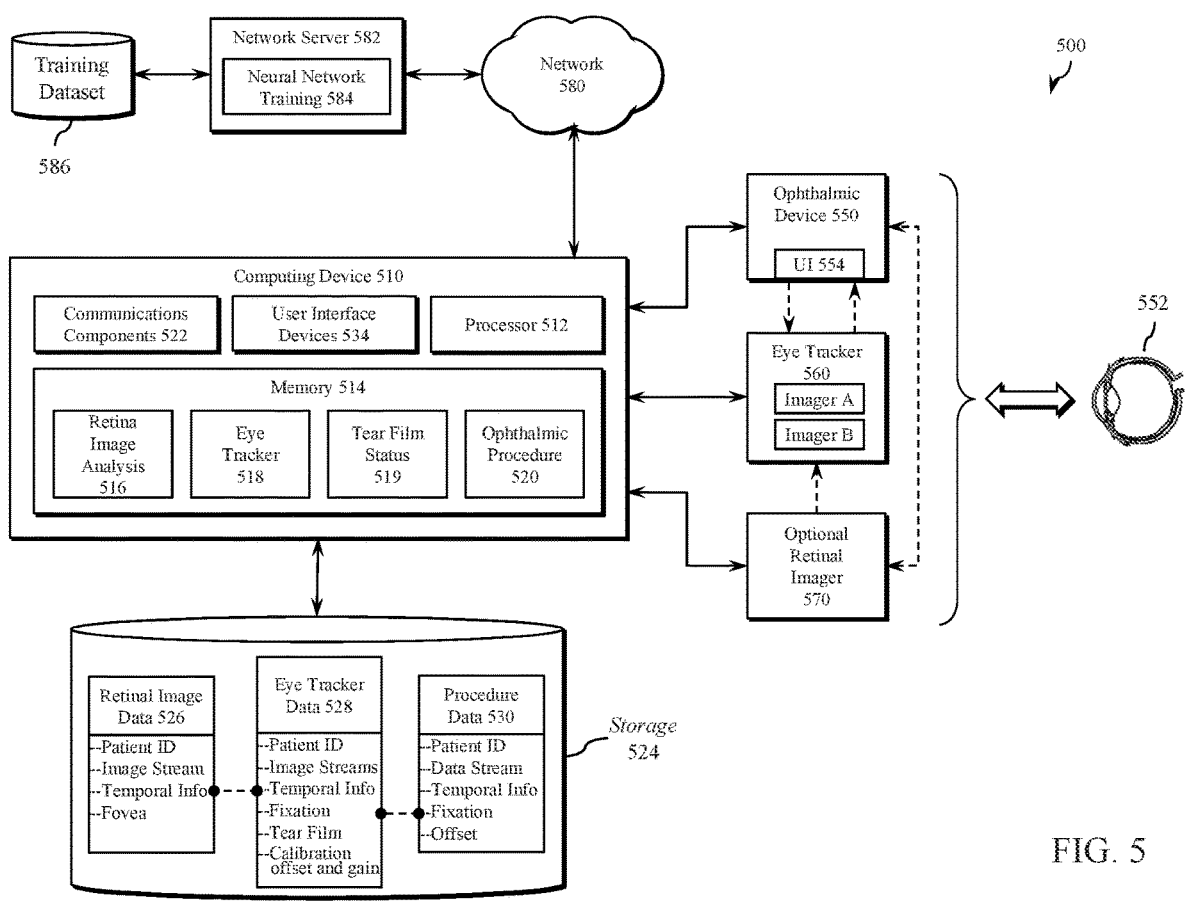
FIG. 5 illustrates an example computing system, in accordance with one or more embodiments of the present disclosure.

Sensor data may be provided to a processor (e.g., as illustrated in FIG. 5) which collects and stores the data in a memory. The processor may use a fusion algorithm to derive a 3D model of the eye comprising a parameterized model that incorporates the various sensor data. The 3D model may be used, for example, for cataracts and corneal refractive surgery planning. The data may be used for ray tracing, to assist in intraocular lens (IOL) implant placement in the eye, etc. The fovea detection and eye tracking innovations described herein may be used with any diagnostic device or instrument that includes a device that scans through the retina. Eye tracking may be implemented in a keratometer, biometer, wavefront measurement device, and other devices including a digital camera and illumination.

In various embodiments, the absolute eye orientation utilizes a device that scans through the retina, such as an OCT device, which may include biometers and other devices that (i) provide retina scanning and other diagnostic modes, and (ii) other sensors that perform other input functions. The system disclosed herein may be used with more components, different components, and fewer components in various embodiments.

Advantages of the present application will be understood by those skilled in the art. The systems and methods disclosed herein provide automated initialization and calibration of eye tracking information that is calibrated to the patient's eye. Eye tracking may be performed when the patient is fixating and not fixating, independent of the patient (e.g., not relying on the patient's cooperation), and may include tracking the tear film status of the eye. The eye tracking information is collected and provided to a logic device, which enables further analysis. Other sensor data may be acquired and validated by backtracking through the data to adjust for a known or projected orientation based on the eye tracking data. For example, an eye position may be determined and provided to the retina imaging system for use in analyzing the scan data. The ability to flag whether the patient is fixation or not fixating is valuable for many system operations and the accuracy provided by the initialization and calibration of the present disclosure allows a system to more accurately determine fixation times/intervals and/or adjust for calculated offsets. The ability to determine a degree of fixation allows the system to adapt for use in variety of implementations. Storing the captured data for later retrieval and analysis allows for further calculations offline and more complex analysis and options, such as through use of complex neural networks or other analytical processes.

In one embodiment, the control logic is configured with a reference point and a threshold which are used to filter out unreliable sensor data. For example, the system may be configured such that a small gaze change (e.g., 0.03 degrees of offset) may be okay, but a larger gaze change will indicate unreliable data that should be filtered out. In some embodiments, the sensor data acquired during fixation may be averaged together or otherwise combined. In other embodiments, the acquired data may be analyzed along with eye position and orientation information by calculating an eye position during acquisition using a calculated offset and known eye position and orientation at a reference point. In some embodiments, the various sensor and data inputs and calculations may be processed using a fusion engine to generate desired output data.

Figure 4:
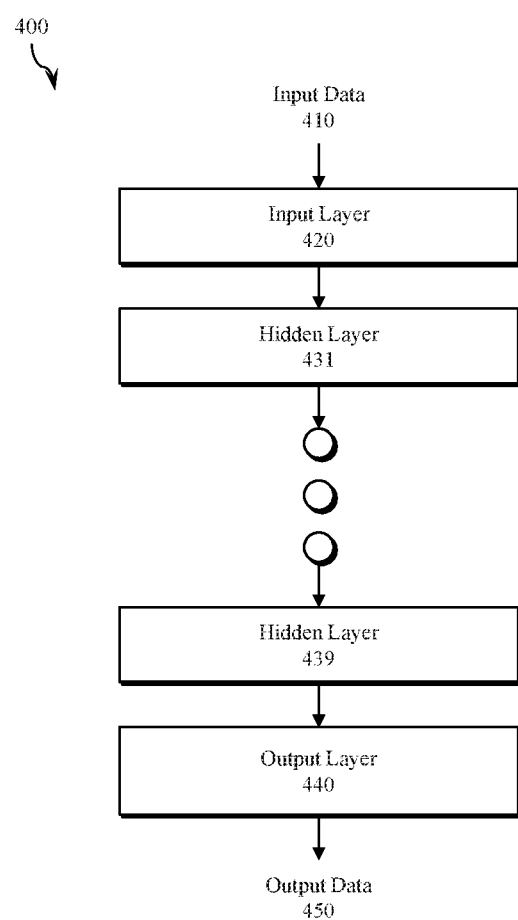
FIG. 4 illustrates an example neural network, in accordance with one or more embodiments of the present disclosure.

In various embodiments, one or more neural networks may be used for image and data analysis, such as to determine whether the eye is fixated on a target object. FIG. 4 is a diagram of an example multi-layer neural network 400 according to some embodiments. The neural network 400 may be representative of a neural network used to implement at least some of the logic, image analysis and/or eye fixation determination logic as described herein. The neural network 400 processes input data 410 using an input layer 420. In some examples, input data 410 may correspond to image capture data and captured retina image data as previously described herein. In some embodiments, the input data corresponds to input training data used to train neural network 400 to make fixation, orientation and/or other determinations.

Input layer 420 includes a plurality of neurons that are used to condition input data 410 by scaling, range limiting, and/or the like. Each of the neurons in input layer 420 generates an output that is fed to the inputs of a hidden layer 431. Hidden layer 431 includes a plurality of neurons that process the outputs from input layer 420. In some examples, each of the neurons in hidden layer 431 generates an output that collectively are then propagated through one or more additional hidden layers that end with hidden layer 439, as illustrated. Hidden layer 439 includes a plurality of neurons that process the outputs from the previous hidden layer. The outputs of hidden layer 439 are fed to an output layer 440. Output layer 440 includes one or more neurons that are used to condition the output from hidden layer 439 by scaling, range limiting, and/or the like. It should be understood that the architecture of neural network 400 is representative only and that other architectures are possible, including a neural network with only one hidden layer, a neural network without an input layer and/or output layer, a neural network with recurrent layers, and/or the like.

In some examples, each of input layer 420, hidden layers 431-439, and/or output layer 440 includes one or more neurons. In some examples, each of input layer 420, hidden layers 431-439, and/or output layer 440 may include a same number or a different number of neurons. In some examples, each of the neurons takes a combination (e.g., a weighted sum using a trainable weighting matrix W) of its inputs x, adds an optional trainable bias b, and applies an activation function $f$ to generate an output a as shown in the equation $a=f(Wx+b)$. In some examples, the activation function $f$ may be a linear activation function, an activation function with upper and/or lower limits, a log-sigmoid function, a hyperbolic tangent function, a rectified linear unit function, and/or the like. In some examples, each of the neurons may have a same or a different activation function.

In some examples, neural network 400 may be trained using supervised learning where combinations of training data that include a combination of input data and a ground truth (e.g., expected) output data. Differences between the generated output data 450 and the ground truth output data may be fed back into neural network 400 to make corrections to the various trainable weights and biases. In some examples, the differences may be fed back using a back-propagation technique using a stochastic gradient descent algorithm, and/or the like. In some examples, a large set of training data combinations may be presented to neural network 400 multiple times until an overall loss function (e.g., a mean-squared error based on the differences of each training combination) converges to an acceptable level. The trained neural network may be stored and implemented in an ophthalmic device (e.g., system 300 of FIG. 3) for real time classification of captured images (e.g., as fixated or not fixated), and/or stored and implemented in an offline system for analysis of the captured data.

FIG. 5 illustrates an example computing system that may include one or more components and/or devices of systems 100, 200 and 300, including an implementation of an eye tracking module 310 and an optional retina imaging system 330. The computing system 500 may include one or more devices in electrical communication with each other, including a computing device 510 that includes a processor 512, a memory 514, communications components 522 and user interface devices 534.

The processor 512 may be coupled to various system components via a bus or other hardware arrangement (e.g., one or more chipsets). The memory 514 may include a read only memory (ROM), a random-access memory (RAM), and/or other types of memory (e.g., PROM, EPROM, FLASH-EPROM, and/or any other memory chip or cartridge). The memory 514 may further include a cache of high-speed memory connected directly with, in close proximity to, or integrated as part of processor 512. The computing device 510 may access data stored in ROM, RAM, and/or one or more storage devices 524 through a cache for high-speed access by the processor 512.

In some examples, memory 514 and/or storage device 524 may store one or more software modules (e.g., software modules 516, 518, and/or 520), which may control and/or be configured to control processor 512 to perform various actions. Although the computing device 510 is shown with only one processor 512, it is understood that processor 512 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, computing device 510 may be implemented as a stand-alone subsystem and/or as a board added to a computing device or as a virtual machine.

To enable user interaction with system 500, the computing device 510 includes one or more communication components 522 and/or one or more user interface devices 534 facilitating user input/output (I/O). In some examples, the one or more communication components 522 may include one or more network interfaces, network interface cards, and/or the like to provide communication according to one or more network and/or communication bus standards. In some examples, the one or more communication components 522 may include interfaces for communicating with computing device 510 via a network 580, such as a local area network, a wireless network, the Internet or other network. In some examples, the one or more user interface devices 534 may include on or more user interface devices such as keyboards, pointing/selection devices (e.g., mice, touch pads, scroll wheels, track balls, touch screens), audio devices (e.g., microphones and/or speakers), sensors, actuators, display devices, and/or other input/output devices.

According to some embodiments, the user interface devices 534 may provide a graphical user interface (GUI) suitable for aiding a user (e.g., a surgeon and/or other medical personnel) in the performance of the processes disclosed herein. The GUI may include instructions regarding the next actions to be performed, diagrams of annotated and/or un-annotated anatomy, such as pre-operative and/or post-operative images of an eye, requests for input, and/or the like. In some examples, the GUI may display true-color and/or false-color images of the anatomy, and/or the like.

The storage device 524 may include non-transitory and non-volatile storage such as that provided by a hard disk, an optical medium, a solid-state drive, and/or the like. In some examples, the storage device 524 may be co-located with computing device 510 (e.g., a local storage device) and/or remote from system 500 (e.g., a cloud storage device).

The computing device 510 may be coupled to one or more diagnostic, imaging, surgical and/or other devices for use by medical personnel. In the illustrated embodiment, the system 500 includes an ophthalmic device 550, an eye tracker 560 and an optional retinal imager 570, which may be embodied in one or more computing systems, including computing device 510. The ophthalmic device 550 includes a user interface 554 for controlling and/or providing feedback to an operator conducting a procedure on a patient's eye 552. The ophthalmic device 550 may include devices for imaging, measuring, diagnosing, tracking, and/or surgically correcting and/or repairing the patient's eye 552.

The ophthalmic device 550 is communicably coupled to the eye tracker 560 (such as eye tracking module 310 of FIG. 3), which receives eye imaging data from the ophthalmic device, and provides status information of the position and alignment of the eye 552 during a procedure. The eye tracker 560 includes two or more imagers (e.g., imager A and imager B) positioned at known locations relative to an optical axis of the ophthalmic device 550. The eye tracker 560 is configured to perform an initialization and calibration procedure that may be fully or partially automated. The calibration procedure includes instructing each of imager A and imager B to capture one or more images of the eye 552 while the eye is fixating, and calculating a calibration offset and gain. The eye tracker 560 may then capture images of the eye 552, analyze the captured images for one or more eye characteristics, and calculate an eye gaze azimuth GA and an eye gaze elevation GE using the calibration offset and gain. The optional retinal imager 570 is communicably coupled to both the ophthalmic device 550 and the eye tracker 560 and configured to capture a retinal image of the eye 552 for use in an ophthalmic procedure and for detection of the fovea for use in fixation tracking.

In various embodiments, the memory 514 includes an optional retina image analysis module 516, an eye tracker module 518, tear film status module 519, and an ophthalmic procedure module 520. The retina image analysis module 516 includes program instructions for instructing the processor 512 to capture retina images using the retinal imager 570 and/or analyze captured retina images. The retina image analysis module 516 may include a neural network trained to receive one more captured retinal images (e.g., a captured image, a real-time stream of retinal images, stored retina images, etc.), extract relevant image features, and detect the presence or absence of the fovea (e.g., output a classification indicting fovea detection, output a probability of proper eye position and/or alignment, etc.).

The eye tracker module 518 includes program instructions for instructing the processor 512 to capture images of the eye 552 using the eye tracker 560 and/or analyze captured images. The eye tracker module 518 may include one or more neural networks trained to receive one or more captured images (e.g., a captured image, a real-time stream of eye images from eye tracker 560, image pairs from image A and image B, stored eye images, etc.), extract relevant images features, and output eye tracking information (e.g., output an indication of eye alignment, output a probability of proper eye position and/or alignment, output an offset of the eye from a proper position and alignment, etc.).

In various embodiments, the eye tracker module 518 is configured to determine a reference eye position based on alignment data received during fixation of the eye 552 on a known fixation point. For example, the eye tracker module 518 may receive fovea detection information from the retina image analysis module 516, which is used to identify corresponding images from the eye tracker 560 that show the eye 552 in proper alignment. The eye tracker module 518 may receive fixation information from other sources, including operator feedback, statistical analysis, image analysis, and other sources available to the system 500. The eye tracker module 518 is further configured to automatically calibrate eye position calculations for the patient's eye by a process including capturing an image from imager A during fixation, capturing an image from imager B during fixation, determining at least one eye characteristic in each image, comparing image coordinates of the eye characteristic(s) in the two images, and calculating a calibration offset and gain for the patient's eye 552 for use in future eye position calculations. The eye tracker module 518 is further configured to analyze images captured by the eye tracker 560 and output eye tracking information with reference to the reference image and/or calculated position.

The tear film status module 519 is configured to analyze images captured by the eye tracker 560, such as images from a camera (e.g., imager A) that is aligned with an optical axis of the device. The tear film status module 519 receives an image sequence from the eye tracker and analyzes the images to determine one or more tear film status events, which may include a blink, an eye open event, and eye closed event, etc. For example, it may be desirable to differentiate between inadvertent blinking and an attempt by the patient to start a measurement sequence. In some embodiments, a blink sequence is defined such a two or more blinks in a row, one or more intentional blinks or long blinks during which the patient ensures a period in which the eye is closed can be detected by the tear film status module 519. In one approach, the tear film status module 519 detects one or more eye characteristics (e.g., pupil center, reflection of illumination source) in the image sequence (e.g., eye opened), detects the obstruction of the one or more eye characteristics (e.g., eye closed), and subsequently detects the present of the one or more eye characteristics (e.g., eye opened again). In various embodiments, the tear film status module 519 may include one or more trained neural networks configured to receive the image stream and output tear film status event.

In some embodiments, the tear film status module 519 interfaces with one or more user interface devices 534 to aid in the process. For example, the film status module 519 may instruct the user interface devices 534 (e.g., a loudspeaker) to generate a beep or other sound to indicate that a blink has been detected. The film status module 519 may further instruct the user interface devices 534 to generate a second sound, such as two beeps, when the blink and/or blink sequence has been detected and the measurement process is underway. In this approach, the patient is informed that the measurement process has begun, which reinforces that to the patient the need to fixate.

The ophthalmic procedure module 520 includes program instructions for instructing the processor 512 to conduct an ophthalmic procedure and may include user input and output during the procedure through user interface 554, and analysis of captured data. In some embodiments, the ophthalmic procedure module 520 includes a trained neural network for analyzing data captured during the procedure. The ophthalmic procedure module 520 receives eye tracking information from the eye tracker module 518, which may include an alignment status within an acceptable offset threshold, offset data, and/or other information. In some embodiments, the ophthalmic procedure module 520 is configured to operate when the patient's eye 552 is in an acceptable alignment position and tear film status, and provide the patient with an indication (e.g. a sound such as a beep, a visual indication such as a flashing light, etc.) through the user interface 554 that the procedure has begun. The ophthalmic procedure module 550 may further provide the operator with an indication when the patient's eye is out of alignment and/or the tear film status needs refreshing.

The system 500 may store captured retinal, eye tracking, tear film, and ophthalmic procedure data for later processing, including online processing (e.g., during a subsequent procedure) and offline processing. The storage device 524 may store retinal images data 526 captured for a patient, which may include a patient identifier, a stream of captured images, temporal information (e.g., a time stamp, sequential index, etc.) and/or information on whether the fovea was detected in an image. The storage device 524 may also store eye tracker data 528, which may include a patient identifier, a stream of captured images, temporal information (e.g., a time stamps, sequential index, etc.), whether the captured image corresponds with a detected fixation period and/or information providing a reference position of an eye during fixation, and/or calibration offset and gain information. The storage device 524 may also store procedure data 530 captured for a patient during the procedure, including a patient identifier, a stream of data captured during the procedure (e.g., images, data readings, data calculations, etc.), temporal information (e.g., a time stamp, sequential index, etc.), offset information calculated for the eye position at a point in the procedure, and/or whether the eye was fixated at a time during the procedure.

The computing device 510 may communicate with one or more network servers 582 providing one or more application services to the computing device. In some embodiments, the network server 582 includes a neural network training module 584 for training one or more of the neural networks using a training dataset 586, which may include labeled images. For example, the retina image analysis module 516 may include a neural network trained using a set of retina images labeled to identify the presence and/or absence of the fovea. The eye tracker module 518 may further include a neural network trained using a set of captured eye images and reference data, labeled to identify an offset of the image with respect to the reference data. The ophthalmic procedure module 520 may include a neural network trained using a set of data representing data captured during a procedure, including alignment and/or offset data from the eye tracker module 518.

Figure 6A:
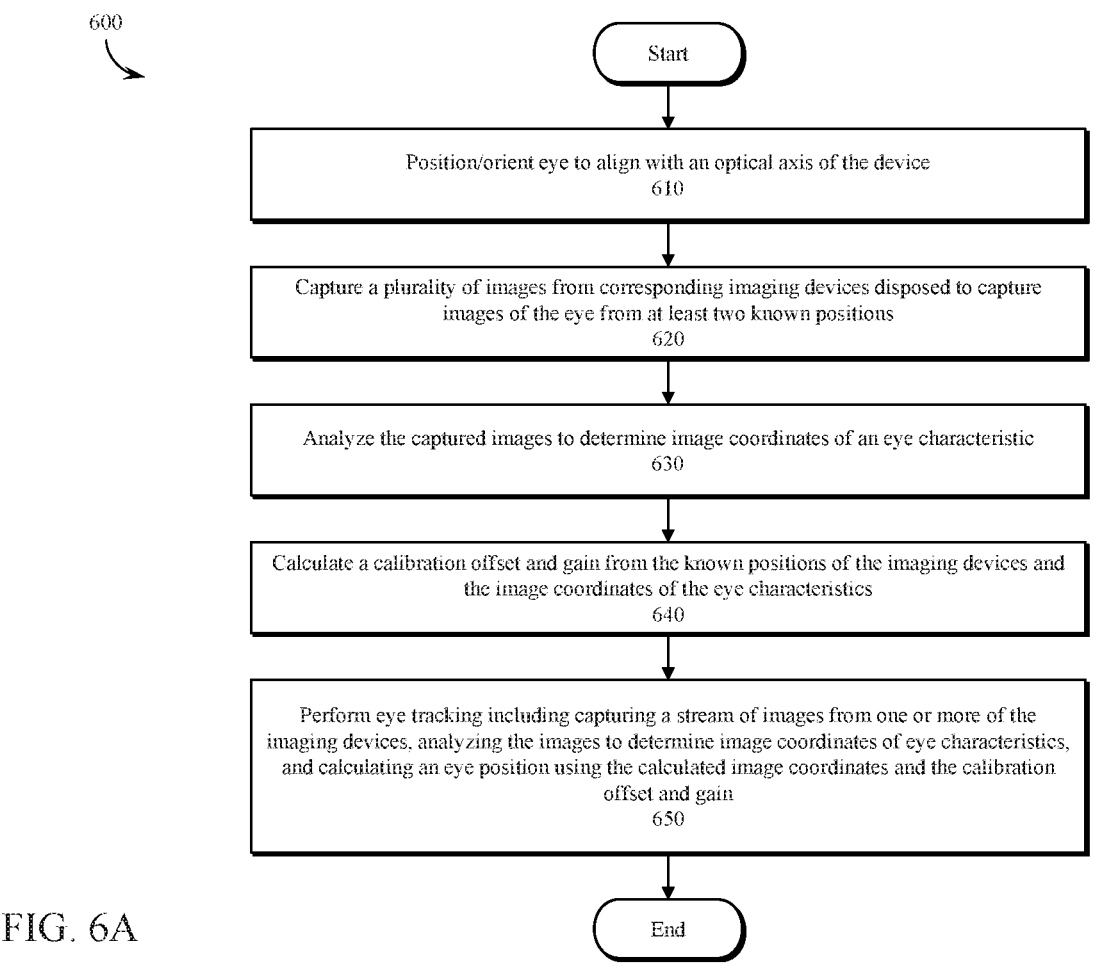
FIG. 6A illustrates an example operation of an automatic initialization and calibration system, in accordance with one or more embodiments of the present disclosure.

Referring to FIG. 6A, an example embodiment of a process 600 for initializing and calibrating an ophthalmic device will now be described. In step 610, the patient is positioned at the ophthalmic system and directed to focus on a target object to align the patient's line of sight with an axis of alignment of the ophthalmic device. In one embodiment the patient's retina is analyzed to confirm the patient is properly fixating. For example, system may include a retina imaging system configured to scan the retina, acquire scanned retina data, and analyze the acquired data to detect the fovea. In some embodiments, the system operator may provide feedback to the system based on the operator's determination of whether the patient is fixating. In other approaches, image data may be acquired during the fixation procedure and analyzed to determine fixation (e.g., through an analysis of histograms or other image data).

In step 620, a plurality of images of the surface of the eye are captured from corresponding imaging devices disposed to capture images from at least two known positions. For example, in the systems of FIGS. 2 and 3, two cameras are used to capture a pair of images of the eye, each from a different known position. In various embodiments, the images are captured simultaneously or sequentially across a short time interval to capture a current position and orientation of the eye.

In step 630, the captured images are analyzed to determine image coordinates of one or more eye characteristic. The eye characteristic may include a center of the pupil detected in the images, center of a cornea detected in the images, location of reflection from an illumination source detected in the images, or other eye characteristic. In some embodiments, the image coordinates represent (x,y) coordinates of a pixel location within each image, which may be mapped to a real world position to determine the eye position and orientation.

In step 640, a calibration offset and gain are calculated from the known positions of the imaging devices and the image coordinates of the eye characteristics. For example, image coordinate differences between two eye characteristics (e.g., pupil center PC and corneal reflection CR location) may correspond to the azimuth (Dx=CRx−PCx) and elevation (Dy=CRy−PCy) of the eye gaze. To more accurately derive the eye gaze azimuth GA and the eye gaze elevation GE from the coordinate differences (e.g., Dx and Dy), a calibration offset value and gain value may be used:

$$GA = ax + bx * Dx$$

$$GE = ay + by * Dy$$

The systems of equations from two imaging devices is used to solve for the calibration offset a and calibration gain b values.

In step 650, the system performs eye tracking during an ophthalmic procedure. The eye tracking includes capturing a stream of images from one or more of the imaging devices, analyzing the images to determine image coordinates of detected eye characteristics, and calculating an eye position and rotation using the calculated image coordinates and calibration offset and gain values. In some embodiments, the calibration offset and gain for the patient's eye and a patient identifier are stored in a lookup table or other storage device and may be accessed and used in subsequent ophthalmic procedures.

Figure 6B:
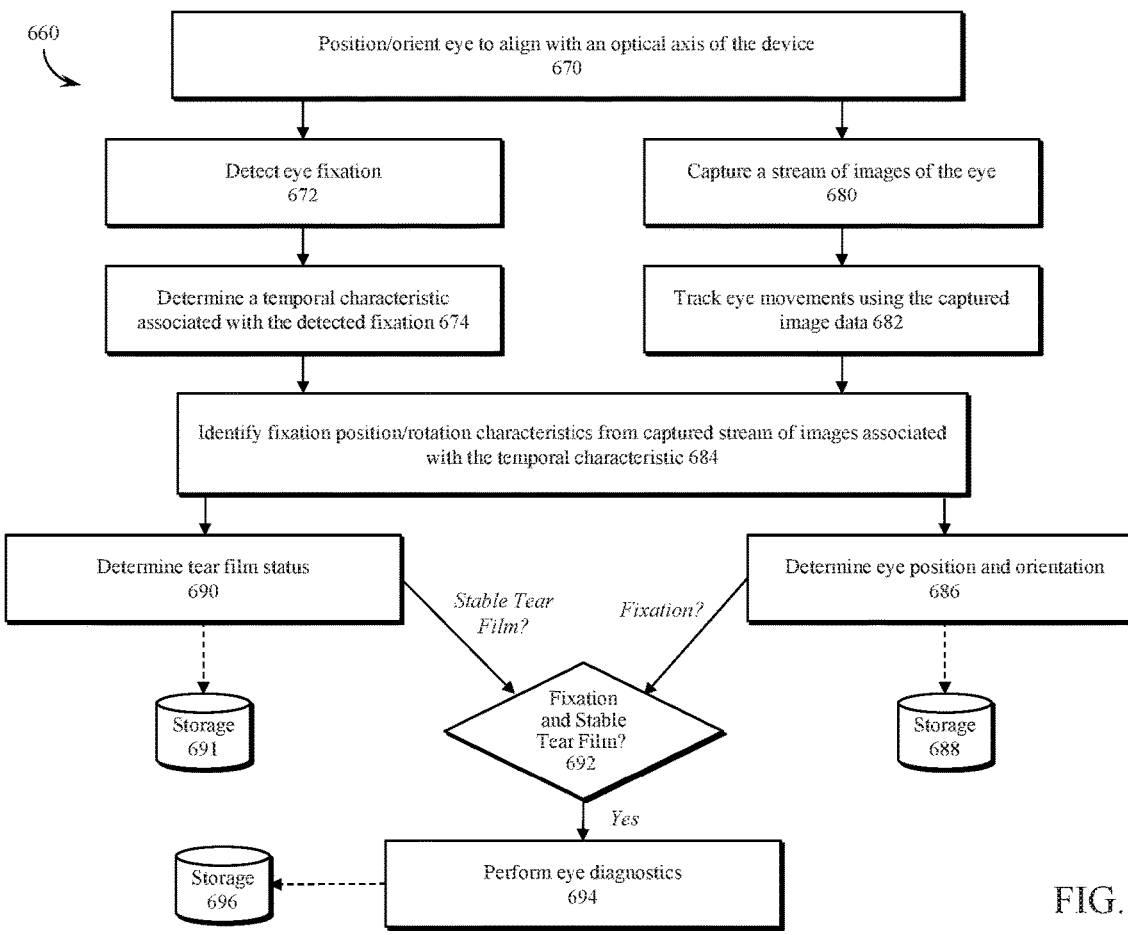
FIG. 6B illustrates an example operation of an eye tracker system, in accordance with one or more embodiments of the present disclosure.

Referring to FIG. 6B, an example process 660 for operating a diagnostic system will now be described in accordance with one or more embodiments. In step 670, the patient is positioned at the ophthalmic system and directed to focus on a target object to align the patient's line of sight with an axis of alignment of the ophthalmic device. In step 672, the system detects eye fixation, which may be performed by an operator, by a retina image system to detect the fovea, through a histogram or other statistical analysis, or through another process. In one embodiment, the ophthalmic system includes a retina imaging system (such as retina imaging system 330 of FIG. 3) configured to scan the retina, acquire scanned retina data, and analyze the acquired data to detect the fovea. In some embodiments, the fovea is visible in the center of the OCT image if the eye is fixating. In step 674, a temporal characteristic associated with the fixation detection is determined. In various embodiments, the temporal characteristic may include a timestamp, a sequential image index, or other criteria allowing synchronization of detected eye fixation with the captured stream of images captured by an eye tracking system.

Simultaneously, an eye tracking system captures a stream of images of the eye in step 680 and tracks the eye movement using the captured image data in step 682. In step 684, the captured image or images matching the temporal characteristic are identified and analyzed to determine a position and orientation of the eye when fixated on the target object.

In step 686, the eye tracker analyzes the stream of captured images against the fixation position (e.g., a reference position) and determines whether the eye is properly fixated within an error threshold. The images and fixation information may be stored (e.g., in storage 688) for later processing. Simultaneously, in step 690, the tear film status is determined. In one embodiment, the images captured by the eye tracker are analyzed to detect a blink or other eye open/eye closed/eye open event. For example, the images may be analyzed to determine the presence of one or more eye characteristics indicating that the eye is open, an obstruction of the one or more eye characteristics indicating the eye is closed, and the reemergence of the one or more eye characteristics in the image stream indicating the eye is open. The tear film status may include detecting a blink event, waiting for a delay period, entering a stable tear film state for an interval of time, and then exiting the stable film state. The tear film data may be stored (e.g., in storage 691) for later processing.

If the eye is properly fixating and the tear film status is stable (step 692), then diagnostics are performed in step 694, which may include eye measurements and other diagnostic data. In some embodiments, the analysis of the retina (step 672) and determination of temporal characteristics associated with the detected fovea (step 674) are performed by a retina imaging system, which is disabled during the eye diagnostics of step 694. Thus, the retina imaging system is not available to track the eye position during the diagnostic procedure.

During the measurement in step 694, the eye tracking system tracks the position and orientation of the eye in step 686 to determine whether the eye is properly positioned and aligned during measurement. In some embodiments, the eye tracking system focuses on the front side of the cornea or inside of the chamber. The eye tracking system may analyze captured images of the eye during the diagnostics (step 694) and determine a current position and rotation based on the captured images. The current position and rotation is compared with the fixation position and rotation to determine an offset. If the offset is below an error threshold, then the eye is determined to be in proper position and alignment for measurement. If the offset is above an error threshold, then the diagnostic process and/or the system operator may be notified that the eye is out of alignment allowing the operator to pause the diagnostic procedure and instruct the patient to reposition the eye, allowing for the associated measurement data to be determined valid/invalid, or allowing for other actions to be taken. In some embodiments, the data acquired during the eye diagnostic procedure (step 694) is stored in a storage device 696 for subsequent processing and analysis.

The retina imaging information and/or fovea detection information may not always be available for use in eye tracking. Some ophthalmic devices, for example, do not include an OCT retina scanner. In some procedures, the fovea may not have been reliably detected before the start of the procedure (e.g., the patient wasn't properly fixating, the fovea wasn't detected in the image with a satisfactory degree of certainty, operator or system error, etc.). In these embodiments, the absolute fixation position may be determined based at least in part on an analysis of images captured from the eye tracker (e.g., images of the surface of the eye). In other embodiments, absolute fixation position may be determined through one or more of operator feedback, detailed initialization procedures, image analysis, statistical analysis and/or other methods.

In various embodiments, a fixation analysis is performed by detecting eye positions in a stream of images captured from a camera and analyzing the results to estimate an absolute fixation position. The analysis may include a statistical analysis using a histogram of eye positions determined from the captured images. If the histogram shows a clear maximum according to the analysis, then the method can estimate the absolute fixation position. If the histogram shows no clear maximum, then the method may indicate that no fixation has been detected. In some embodiments, the analysis of the captured images may include a comparison between the patient's eye and other eyes in known positions (e.g., use of a neural network trained using a set of labeled training images), historical fixation information for the patient, image analysis (including tolerances/thresholds), and/or other analysis of available information. In some embodiments, the method may rely on the operator and patient to properly fixate the patient's eye. In some embodiments, the method may address scenarios in which the operator and/or patient error causes the images to not reflect fixation (e.g., if the patient fixates intentionally on a wrong spot, or the operator doesn't properly instruct and/or monitor the patient).

Embodiments of systems and methods for eye tracking in which a retina OCT scan is not available and/or the fovea has not been reliably detected before the procedure will now be described with reference to FIGS. 7-10. As previously discussed, an accurate measurement of the eye using an ophthalmic device may start with an alignment of the patient's line-of-sight (the patient's visual axis) to a certain optical axis of the ophthalmic device. The line-of-sight in this context may be the axis along which the patient looks at things. The resulting diagnostic data and/or other results of the ophthalmic procedure may be unreliable during the periods in which the patient was not properly fixating.

The absolute eye fixation position may be used by the ophthalmic device to provide feedback to a device operator regarding whether the patient is fixating (or not properly fixating) on a certain optical axis of a diagnostic device during a procedure (e.g., a measurement procedure). The ophthalmic device may use the absolute eye fixation position during the procedure to identify periods during which the patient is properly fixating. The system may also use the absolute eye fixation position to determine whether data acquired during a procedure is reliable and/or unreliable data based at least in part on whether the patient was determined to be fixating during data acquisition.

Figure 7:
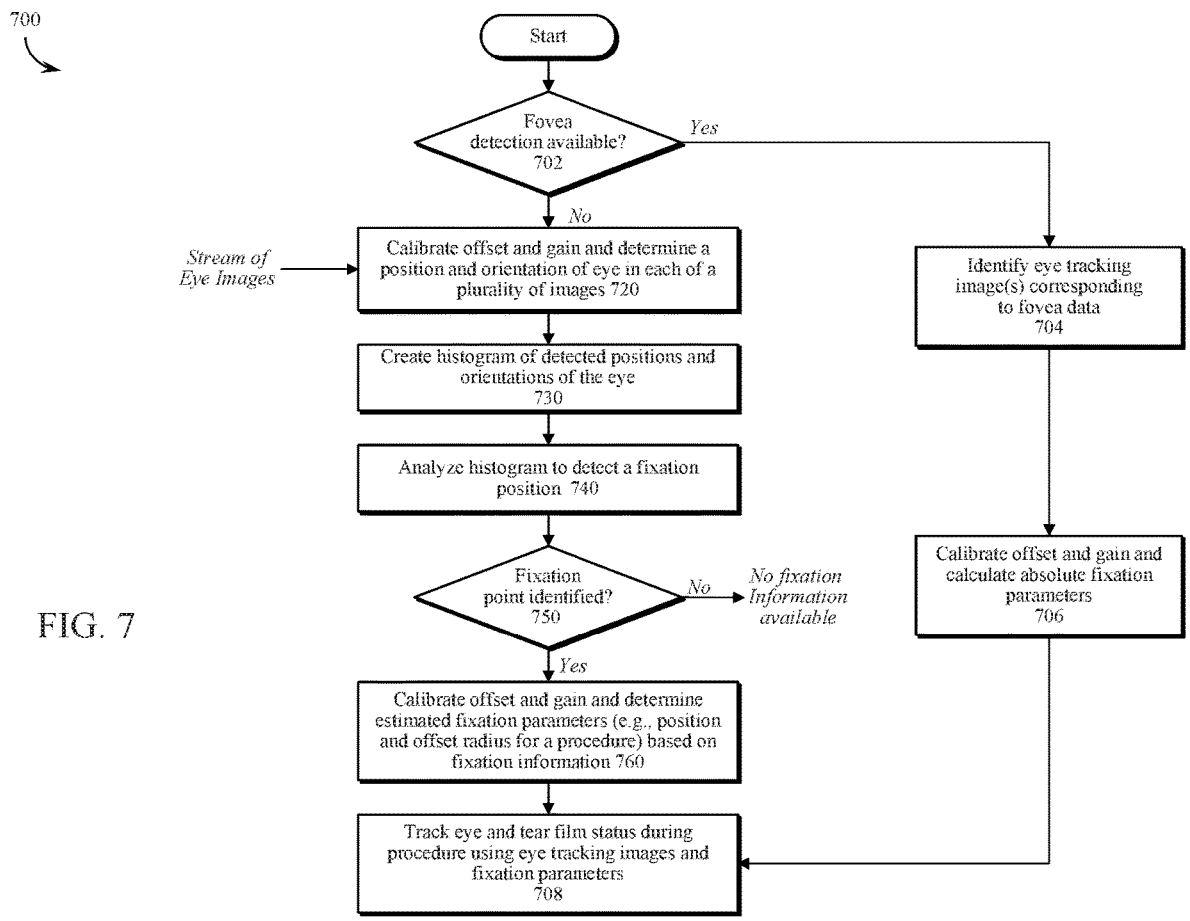
FIG. 7 illustrates a method for estimating an absolute eye position, in accordance with one or more embodiments of the present disclosure.

Referring to FIG. 7, an embodiment of a method 700 for estimating absolute eye fixation will now be described. The method 700 is performed using a computing device and an imaging system that may include a camera and an illumination system (e.g., imaging devices 312 and 313 and illumination components 314 of FIG. 3) for imaging the surface of a patient's eye. The method determines the position and orientation of the eye by using the position of detectable features of the eye in the image (e.g., the pupil, limbus, iris features, etc.) and the position of the reflection of the illumination system at the cornea. The position of the eye is determined during a procedure or other time during which the patient is expected to be properly positioned and fixating with reference to an optical axis of the ophthalmic device. The operator may start the process by providing feedback (e.g., by pressing one or more buttons) and/or the operator may start the sequence which is then followed by the patient. Optionally, the operator may provide confirmation of the patient's compliance with the procedure.

The method 700 illustrates an embodiment for implementation by a computing device of an ophthalmic device that may include a retina OCT imaging device. To determine an absolute fixation position, the computing system determines whether fovea detection information is available (step 702). Fovea detection information may be available, for example, if the ophthalmic device includes a retina imaging device that scanned the patient's eye while the patient was properly fixating. If fovea detection information is available, the method proceeds to step 704 where the computing system identifies eye tracking images that correspond to the detected fovea data (e.g., as described above with reference to FIG. 3). In step 706, the system calibrates the offset and gain and calculates absolute fixation parameters using the corresponding images. The patient's eye may then be tracked during a procedure using eye tracking images, the fixation parameters and calibrated equations.

Referring back to step 702, if fovea detection is not available then the method uses the captured images of the eye (e.g., images of the surface of the eye) to estimate the absolute fixation parameters. In step 720, the computing device receives a stream of captured images from the camera, calibrates the offset and gain values using at least one pair of images captured from different cameras disposed at known locations, and determines a position and orientation of the eye in each of a plurality of images. The computing device may process each received image or a subset of the received images (e.g., in accordance with processing constraints). The images may be received before/during a procedure and/or after a procedure when analyzing captured data.

After the position and orientation of the eye is determined for a series of captured images, a histogram is generated of the determined positions and orientations in step 730. In some embodiments, the position and orientation information include a pixel position of the center of the pupil in each of the images, which is used to construct a two-dimensional histogram of (x,y) coordinates. The position and orientation information may include an absolute position and orientation of the eye determined from each of the images, which is used to construct a two-dimensional histogram. Other representations of the position and orientation data may also be used (e.g., a heat map) in the present method. In some embodiments, operator feedback may be used to indicate images in which the patient has been instructed to fixate and/or to indicate whether the patient has not been fixating, and the corresponding images can be added to or discarded from the analysis. A procedure may be conducted in which the operator of the system instructs the patient to fixate on an object during a measurement sequence.

Figure 8:
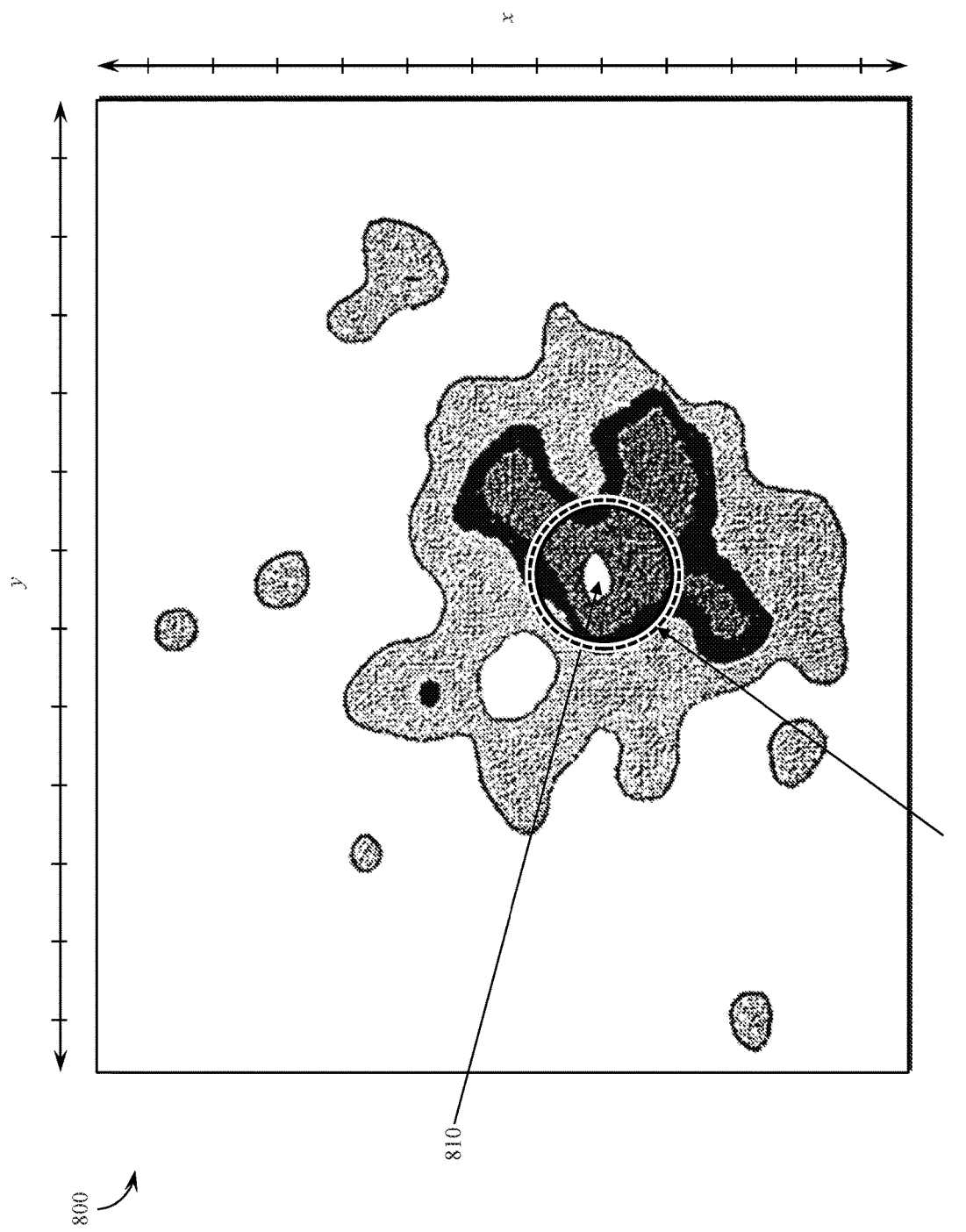
FIG. 8 illustrates an example heat map of eye position and orientation detected using an eye tracker, in accordance with one more embodiments of the present disclosure.

Referring to FIG. 8, a heat map 800 is illustrated showing an example distribution of fixation points the patient has looked at. The map may be color coded, three-dimensional, or otherwise include indicia to track the frequency in which the patient has fixated at certain spots. Other indicators (e.g., a color close to a background color) may be used to indicate a short time of fixation at that spot. In the illustrated embodiment, an area 810 of the heat map shows the most common coordinates and may indicate the position and orientation of the patient's eye while properly fixating on a target object. The dashed circle 820 indicates positions and orientations that are within a threshold offset to be chosen for a fixation determination depending on the level of precision needed for a procedure or analysis.

Figure 9:
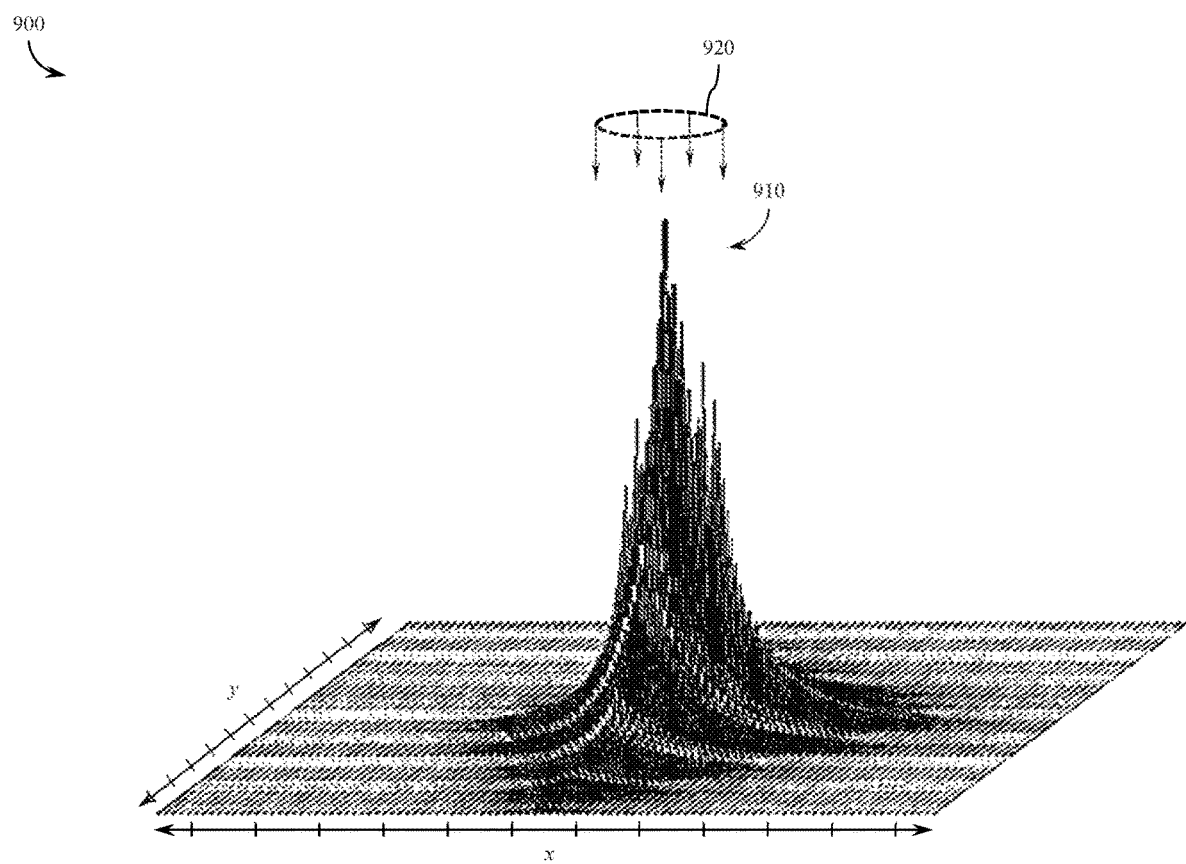
FIG. 9 illustrates an example histogram constructed of eye position and orientation data detected using an eye tracker, in accordance with one or more embodiments of the present disclosure.

FIG. 9 illustrates an example histogram 900 plotting eye coordinates detected from captured images. The maximum of this distribution 910 may be used to estimate the position and orientation of the fixated eye (e.g., by identifying the position and orientation in which the patient was most often fixating). This estimated position and orientation may be used as a reference position for further eye fixation determinations. For example, an analysis of medical data taken in a measurement sequence, may use only the data points acquired when the eye had an orientation and position within an acceptable offset (e.g., as indicated by circle 920) from the reference position (e.g., which is based at least in part on the maximum of the histogram).

As previously discussed, the histogram 900 may be constructed by plotting the fixation points determined from the captured images. For example, the histogram may track eye position as a series of pixel locations of the detected pupil or an otherwise identified center of the eye (e.g., as determined from reflections or other measurements). As the sequence of images is received and analyzed, a pattern may emerge indicating a position in which the patient is most often fixating. In some embodiments the values in the histogram may include an average of adjacent pixels and/or incorporate other smoothing.

Referring back to the method 700 of FIG. 7, in step 740 the histogram is analyzed to detect a fixation position. As previously discussed, the fixation position may relate to a maximum value of the histogram that meets certain analysis criteria. For example, a maximum may be selected based on a variety of factors including a degree of the maximum over the average value, a degree over a threshold value for a given number of images, etc. In some embodiments, the eye tracking continues during the procedure and the maximum/fixation position may be updated in real time as more images are analyzed.

Referring to step 750, if no acceptable maximum is found (or other fixation point criteria met), then eye fixation information is not available through this process. In some embodiments, the eye tracking continues during the procedure and the maximum/fixation position may be identified and/or updated in real time as more images are analyzed.

In step 760, the calibration offset and gain and estimated fixation parameters are determined (e.g., fixation position and offset radius acceptable for a procedure) based on the detected fixation information. The patient's eye may then be tracked during the procedure in step 708, using the eye tracking images and the estimated fixation parameters.

Figure 10:
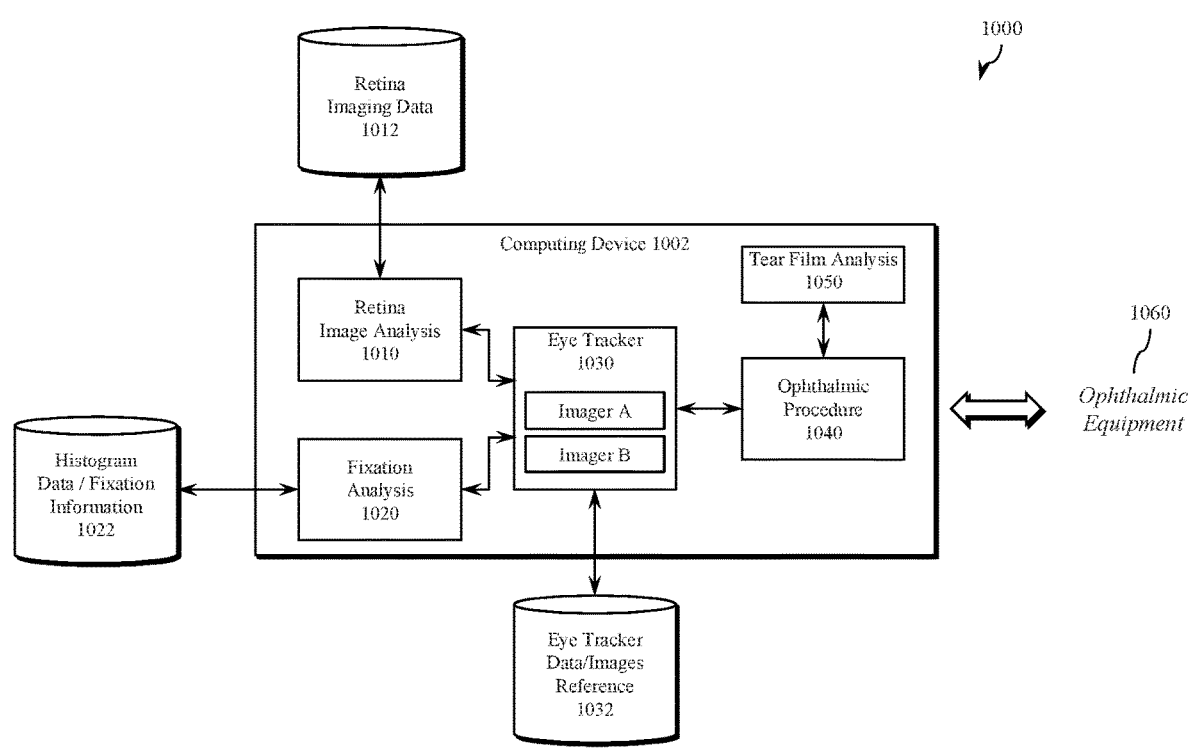
FIG. 10 illustrates an example system for implementing the method of FIG. 7, in accordance with one or more embodiments of the present disclosure.

Referring to FIG. 10, an example system 1000 for implementing the method of FIGS. 7-9 will now be discussed. A computing device 1002 (such as computing device 510 of FIG. 5) is communicably coupled to ophthalmic equipment 1060 and is configured to perform processes associated with an eye tracker 1030, tear film analysis 1050 and an ophthalmic procedure 1040. The computing device 1002 may be configured to perform a retina image analysis (through retina image analysis module 1010) using a retina imaging device (if available) of the ophthalmic equipment 1060 and store retina image data 1012. The computing device 1002 further includes fixation analysis module 1020, for performing an implementation of the method illustrated in FIG. 7 or other method for estimating absolute fixation parameters. In one embodiment, the fixation analysis module 1020 receives and analyzes streams of eye images captured by one or more cameras (e.g., imager A and imager B) of the eye tracker 1030, constructs and analyzes a histogram of fixation positions, and determines reference positions and associated radii. The fixation data, including histogram data, may be saved in a storage 1022 (e.g., a memory or storage device).

In some embodiments, computing device 1002 includes a logic device that is configured to perform program instructions stored in a memory, which may include the fixation analysis module 1020, the optional retina image analysis module 1010, the eye tracker 1030, tear film analysis module 1050 and processes associated with the ophthalmic procedure 1040. The computing device 1002 may also be coupled to a storage device 1032 for storing eye tracker data, images, reference information, and other data.

The fixation analysis module 1020 may be configured to analyze the relative gaze of a patient's eye using images captured by the eye tracker 1030. The fixation analysis module 1020 may calibrate the measurements using a pair of images captured from different cameras to derive a calibration offset and gain, which allows for accurate determination of the eye position and orientation from image pixel coordinates of eye characteristics. The fixation analysis module 1020 may construct a histogram tracking gaze orientation (e.g., pitch and yaw of the eye, relative up/down and left/right offsets, curvature/rotation, etc.) and analyze peak values of the histogram (e.g., the number of data values at each location) to get an estimate of the absolute reference. In some embodiments, the fixation analysis module 1020 estimates an optical axis of the eye and an intersection with the eye tracker camera to track the gaze orientation.

The eye tracker 1030 may be configured to capture, store and process images of the patient's eye. The eye tracker 1030 may be configured to determine a patient's eye position and origination from one or more captured images for further analysis by the fixation analysis module 1020. In some embodiments, each analyzed image may include an x,y position representative of an eye position and orientation (e.g., rotation around the x axis and y axis). The eye tracker may use information about relative orientation changes from one image to another in connection with an absolute fixation position (e.g., determined through retina image analysis 1010) or estimated absolute fixation position (e.g., determined through fixation analysis module 1020). In some embodiments, the fixation analysis module 1020 operates on an assumption that the patient was attempting to fixate most of the time, and that the estimated absolute fixation position can be determined by constructing a histogram of x and y rotation and determining the gaze orientation that is most prominent. In various embodiments, the histogram can be constructed of pixel coordinates, rotation around x and/or y, offset values, or other data. Each image can provide a coordinate pair representing calculated eye gaze orientation which is added to the histogram.

In some embodiments, the fixation analysis module 1020 is configured to analyze the histogram by detecting one distinct peak (e.g., prominent peak surrounded by smaller peaks) and determining a level of confidence that a fixation position has been detected. If no clear peak is detected, then a confidence level may be low. A radius around a detected peak may be used (e.g., humans can fixate plus/minus 0.5 degree). The threshold of peak to average and/or size of the radius may change depending on system and procedure requirements.

The computing device 1002 may include one or more neural networks trained to make one or more determinations disclosed herein, including analyzing histogram data to determine whether an eye fixation position can be determined. In some embodiments, the fixation analysis may further include a comparison of known eye tracking images and/or eye fixation parameters for the patient and/or other patients. For example, one or more images may be input into a neural network trained using historical data to determine whether the eye in an image is fixating.

Figure 11:
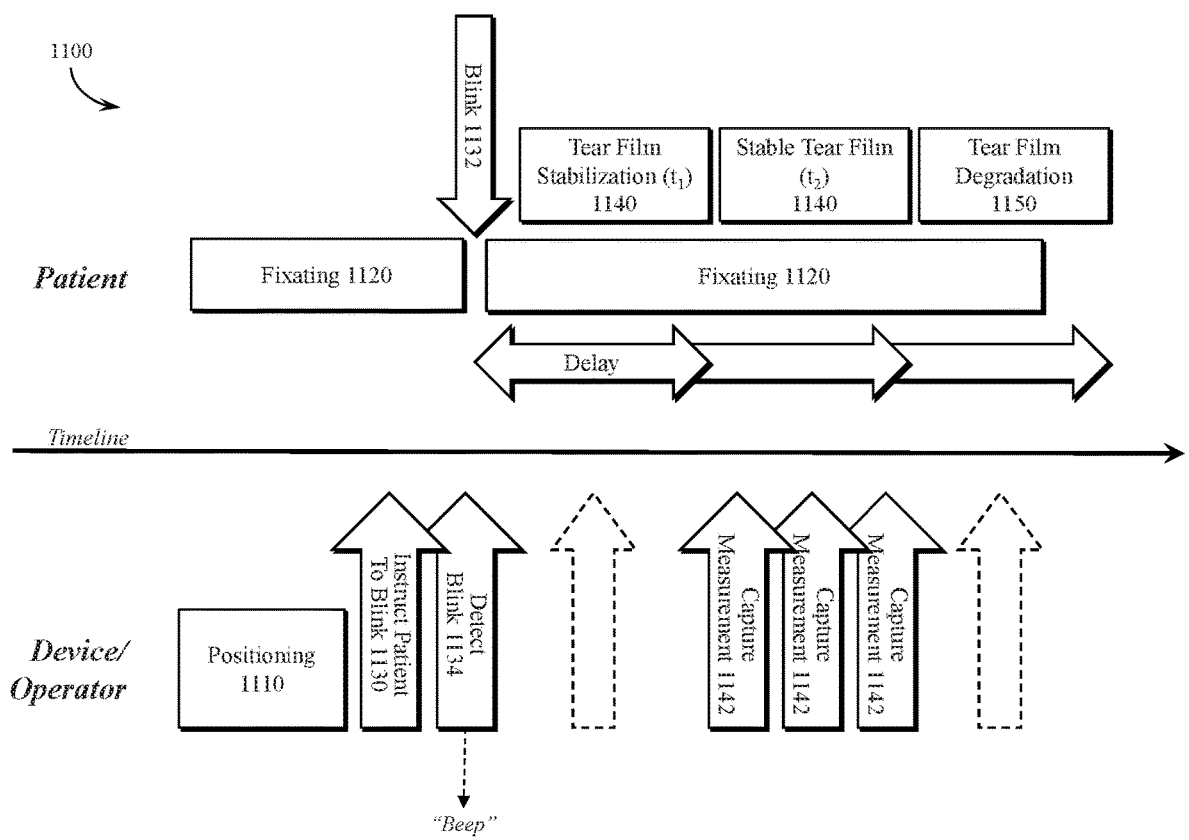
FIG. 11 illustrates an example measurement process, in accordance one or more embodiments of the present disclosure.

Referring to FIG. 11, an example method for tracking the status of the patient's tear film will now be described. The method 1100 includes patient-induced triggering which, in various systems, may be implemented as (i) the patient pressing a button on a user input device, (ii) the system detecting when the patient blinks, and (iii) the system detecting when there is a change in fixation status between fixating and not fixating.

In some embodiments, the system is configured to detect when the patient blinks and when the patient fixating, such that measurements may be taken when the tear film status and fixation status are favorable. In one embodiment, the system is configured to detect the patient blinking by tracking the eye with eye tracker or other system component. This can be achieved with a video-based system or other imaging methods (e.g. optical coherence tomography), one or more trained neural networks, an expert system, and/or other systems and components. The patient is asked to blink in a certain way, e.g. two times, hard blink, etc. The system is configured to detect the event and trigger the measurement acquisition after the tear film is stabilized.

The device can provide feedback to the user (e.g., can emit a beep every time a blink is detected). With the appropriate number of blinks, duration of blinks and a defined delay of the acquisition after the last blink a well-defined measurement condition can be achieved to identify the stable tear film state. This method can be implemented in variety of ophthalmic diagnostic devices that include an imaging system.

In operation, a patient is positioned relative to the device by an operator in step 1110. The patient is instructed to fixate in step 1120 on a target object to align one of the patient's eyes with an optical axis of the device, and the patient attempts to fixate on the target object throughout the procedure. In step 1130, the patient is instructed to blink or perform another eye open/eye close sequence to renew the tear film of the eye. The patient blinks as instructed in step 1132. In some embodiments, the patient is instructed to blink a certain way (e.g., two times in a row) to renew the tear film and signal to the device that blinking has been performed. In step 1134, the device detects the blinking performed in step 1132. In some embodiments, the patient's eye is imaged using an eye tracker to capture a visual representation of the surface of the eye. A stream of images (e.g. a video stream) is analyzed to detect the blinking sequence. For example, a blink detection component may perform an image analysis to detect the pupil of the eye, a reflection of an illumination source off of the eye, or other eye characteristics. The image sequence may be analyzed, for example, to determine an eye open state and an eye closed state. The blinking pattern may be detected by searching for a sequence of blinks (e.g., eye open state→eye closed state→eye open state) within a short time period (e.g., 2 blinks within a 3 seconds). In some embodiments, a trained neural network may be used to detect the eye opened and eye closed states from the captured images.

If a blink sequence is detected in step 1134, then a delay period is started to allow for tear film stabilization in step 1140. In some embodiments, the patient is notified through an audible beep or other indication. After t1 second passes, the device enters the stable tear film state for t2 during which measurements may be captured by the device. During the stable tear film state 1140, the patient continues to fixate on the target object (step 1120). In some embodiments, the device detects whether the patient is properly fixating using an eye tracker or other device components. The eye tracker may capture images of the eye and compare the current position to a reference position to determine whether the eye is fixating within an acceptable offset range. One or more measurements may be captured in step 1142 during the stable tear film state t2 and during a fixation state. After the stable tear film period (step 1140), the tear film is assumed to have degraded to a level that would render captured measurements unreliable (step 1150). At this state, the patient may stop fixating to end the procedure. In some embodiments, the sequence is completed in 2-6 seconds, and may repeat to renew the tear film for additional measurement opportunities.

In various embodiments, the operator may be provided with feedback on whether the patient is or is not fixating on this axis during the data acquisition, even when the retina imaging data is not available (e.g., not part of the system and/or fovea detection not available before procedure). The systems and methods disclosed herein provide a cost-efficient solution that is suitable for use with an ophthalmic diagnostic device that uses an image capture device and an illumination system as described herein.

As will be understood by those skilled in the art, the method of the illustrated embodiment provides improved techniques for independently verifying whether the patient's eye is properly fixating on the target object during operation. By detecting the fovea at a specific point in time, the system may determine where the line of sight/visual axis is located for the patient. This information allows the system to determine whether the patient is currently fixating during a measurement sequence or other diagnostic or corrective procedure. This method combines a system that images the retina and a system that tracks the eye using surface information. From the position of the fovea in the retina image, the system can determine the eye tracking location and determine whether the eye is moving to the left or right/up or down. The system can track the user gaze, calculate an offset, determine current eye position and orientation, make determinations regarding eye fixation, determine data validity, and provide other features in accordance with the present disclosure.

Methods according to the above-described embodiments may be implemented as executable instructions that are stored on non-transitory, tangible, machine-readable media. The executable instructions, when run by one or more processors (e.g., processor 512) may cause the one or more processors to perform one or more of the processes disclosed herein. Devices implementing methods according to these disclosures may comprise hardware, firmware, and/or software, and may take any of a variety of form factors. Typical examples of such form factors include laptops, smart phones, small form factor personal computers, personal digital assistants, and/or the like. Portions of the functionality described herein also may be embodied in peripherals and/or add-in cards. Such functionality may also be implemented on a circuit board among different chips or different processes executing in a single device, by way of further example.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system comprising:
an ophthalmic device configured to measure characteristics of an eye of a patient;
an eye tracker configured to capture a first stream of images of the eye; and
a logic device configured to:
analyze the first stream of images to determine whether the eye is fixating on a target object;
detect a predetermined blink sequence of a plurality of blinks in succession within a pre-determined time in the first stream of images and interpret the predetermined blink sequence of a plurality of blinks in succession within a pre-determined time as a patient-induced trigger of a measurement capture;
after a predetermined tear stabilization period, start a stable tear film interval;
provide an audible sound to the patient when the stable tear film interval begins to reinforce a need to maintain fixation on the target object during the stable tear film interval; and
during the stable tear film interval, capture at least one measurement of the eye using the ophthalmic device when the eye is fixating on the target object.

2. The system of claim 1, further comprising:
detecting the predetermined blink sequence in the first stream of images comprises processing the images through a neural network trained to detect an open eye and/or a closed eye.

3. The system of claim 1, wherein the eye tracker is configured to capture a first image of the eye from a first location and a second image of the eye from a second location; and
wherein the logic device is further configured to:
detect a first plurality of eye characteristics from the first image, the eye characteristics having first corresponding image coordinates;
detect a second plurality of eye characteristics from the second image, the eye characteristics having second corresponding image coordinates; and
determine a calibration offset and a calibration gain based at least in part on the first corresponding image coordinates, the second corresponding image coordinates, the first location and the second location.

4. The system of claim 3, wherein the logic device is further configured to:
determine an eye fixation position and orientation relative to an optical axis of the eye tracker based at least in part on the first corresponding image coordinates and/or the second corresponding image coordinates.

5. The system of claim 1, wherein the logic device is further configured to:
estimate eye fixation parameters based at least in part on the determined eye fixation position and orientation;
receive the first stream of images from the eye tracker; and
track a current eye position and orientation by analyzing at least one image from the first stream of images to determine the current eye position and orientation relative to the eye fixation parameters;
wherein the eye fixation parameters comprise a reference position and orientation of the eye when fixated.

6. The system of claim 1, wherein the logic device is further configured to determine the fixation position relative to an optical axis of the eye tracker by constructing and analyzing a histogram of detected eye positions and orientations;
wherein analyzing the histogram further comprises determining whether coordinates of a relative maximum value comprise a fixation position and orientation; and
wherein determining whether coordinates of the relative maximum value comprise a fixation position and orientation further comprise comparing the relative maximum value with a threshold and/or an average coordinate value of the histogram.

7. The system of claim 1, further comprising:
a retina imaging system comprising an optical coherence tomography (OCT) scanner configured to perform a retinal scan;
wherein the eye tracker is further configured to capture a stream of images of the eye during the retinal scan;
wherein the retina imaging system is further configured to:
capture a plurality of retinal images of the eye;
detect whether a fovea is present in one or more of the plurality of retinal images of the eye; and
identify a first retinal image from the plurality of retinal images of the eye having the detected fovea; and
wherein the logic device is further configured to:
determine a corresponding image from the stream of images having a temporal proximity to the first retinal image; and
analyze the corresponding image to determine eye fixation parameters.

8. The system of claim 1, wherein the logic device is configured to track the eye position and orientation and calculate an offset from eye fixation parameters and determine if the offset is less than a threshold value;
wherein when the offset is less than the threshold value the eye is determined to be fixated and the logic device generates an indication of fixation; and
wherein when the offset is greater than the threshold value the eye is determined to be out of alignment and the control processor generates an indication of no fixation.

9. The system of claim 1, wherein the logic device is further configured to perform an eye diagnostic procedure and track eye position using the eye tracker during the eye diagnostic procedure.

10. The system of claim 1, further comprising a diagnostic device configured to perform an eye diagnostic procedure while tracking a position and orientation of the eye using the eye tracker; wherein the diagnostic device is configured to modify the eye diagnostic procedure based, at least in part, on data representative of eye fixation parameters and a tracked eye position.

11. A method comprising:
capturing, using an eye tracker, a first stream of images of an eye of a patient;
analyzing the first stream of images to determine whether the eye is fixating on a target object;
detecting a predetermined blink sequence of a plurality of blinks in succession within a pre-determined time in the first stream of images and interpret the predetermined blink sequence of a plurality of blinks in succession within a pre-determined time as a patient-induced trigger of a measurement capture;
tracking a stable tear film interval after a predetermined tear stabilization period;
providing an audible sound to the patient when the stable tear film interval begins to reinforce a need to maintain fixation on the target object during the stable tear film interval; and during the stable tear film interval, capturing at least one measurement of the eye using an ophthalmic device when the eye is fixating on the target object.

12. The method of claim 11, further comprising:
processing the images through a neural network trained to detect an open eye and/or a closed eye.

13. The method of claim 11, further comprising:
capturing a first image of an eye from a first location;
capturing a second image of the eye from a second location that is different than the first location;
detecting a first plurality of eye characteristics from the first image, the eye characteristics having first corresponding image coordinates;
detecting a second plurality of eye characteristics from the second image, the eye characteristics having second corresponding image coordinates; and
determining a calibration offset and a calibration gain based at least in part on the first corresponding image coordinates, the second corresponding image coordinates, the first location and the second location.

14. The method of claim 13, further comprising:
capturing a stream of images of the eye;
detecting an eye position and orientation in the stream of images based at least in part on coordinates of the detected eye characteristics, the calibration offset and the calibration gain; and
determining an eye fixation position and orientation relative to an optical axis.

15. The method of claim 14, further comprising:
estimating eye fixation parameters based, at least in part, on the determined eye fixation position and orientation; and
tracking the eye position and orientation by analyzing one or more images from the stream of images to determine the eye position and orientation relative to the eye fixation parameters;
wherein the eye fixation parameters comprise a reference position and orientation of the eye when fixated.

16. The method of claim 11, further comprising training a neural network to receive the stream of images and output a determination of an eye position.

17. The method of claim 11, further comprising detecting the fixation position relative to an optical axis of a device by constructing and analyzing a histogram of detected eye positions and orientations;
wherein analyzing the histogram further comprises determining a relative maximum value.

18. The method of claim 11, further comprising:
performing a retina imaging scan of the eye using an optical coherence tomography (OCT) scanner;
capturing a plurality of retinal images of an eye from the retina imaging scan;
capturing a stream of images using an imaging device configured to image a surface of the eye;
detecting whether a fovea is present in one or more of the plurality of retinal images;
identifying a first retinal image from the plurality of retinal images having the detected fovea;
determining a corresponding image from the stream of images having a temporal proximity to the first retinal image; and
analyzing the corresponding image to determine eye fixation parameters.

19. The method of claim 11, further comprising tracking an eye position and orientation and calculating an offset from eye fixation parameters and determining if the offset is less than a threshold value;
wherein when the offset is less than the threshold value the eye is determined to be fixated and an indication of fixation is generated; and
wherein when the offset is greater than the threshold value the eye is determined to be out of alignment and an indication of no fixation is generated.

20. The method of claim 11, further comprising performing an eye diagnostic procedure while tracking the position and orientation of the eye using the eye tracker; and
modifying the eye diagnostic procedure based, at least in part, on data representative of eye fixation parameters and a tracked eye position.

* * * * *